US012582325B2

(12) United States Patent
Wu et al.

(10) Patent No.: US 12,582,325 B2
(45) Date of Patent: Mar. 24, 2026

(54) CONTACTLESS IMAGE-BASED BLOOD OXYGEN ESTIMATION

(71) Applicants: UNIVERSITY OF MARYLAND, COLLEGE PARK, College Park, MD (US); NORTH CAROLINA STATE UNIVERSITY, Raleigh, NC (US)

(72) Inventors: Min Wu, Clarksville, MD (US); Xin Tian, College Park, MD (US); Joshua Regi Mathew, Durham, NC (US); Chau-Wai Wong, Apex, NC (US)

(73) Assignees: UNIVERSITY OF MARYLAND, COLLEGE PARK, College Park, MD (US); NORTH CAROLINA STATE UNIVERSITY, Raleigh, NC (US)

( * ) Notice: Subject to any disclaimer, the term of this patent is extended or adjusted under 35 U.S.C. 154(b) by 928 days.

(21) Appl. No.: 17/849,414

(22) Filed: Jun. 24, 2022

(65) Prior Publication Data

US 2023/0000377 A1 Jan. 5, 2023

Related U.S. Application Data

(60) Provisional application No. 63/214,641, filed on Jun. 24, 2021.

(51) Int. Cl.
*A61B 5/024* (2006.01)
*G06V 10/25* (2022.01)
(Continued)

(52) U.S. Cl.
CPC .......... *A61B 5/02416* (2013.01); *G06V 10/25* (2022.01); *G06V 10/56* (2022.01);
(Continued)

(58) Field of Classification Search
CPC .... A61B 5/02416; G06V 10/25; G06V 40/11; G06V 40/117; G06V 10/56; G06V 10/82; G06V 40/15; G06V 10/62
See application file for complete search history.

(56) References Cited

U.S. PATENT DOCUMENTS

2022/0240861 A1 * 8/2022 Hoffman .............. A61B 5/6826

OTHER PUBLICATIONS

Moço A, Verkruysse W. Pulse oximetry based on photoplethysmography imaging with red and green light: Calibratability and challenges. Journal of clinical monitoring and computing. Feb. 2021;35(1):123-33. (Year: 2021).*

(Continued)

*Primary Examiner* — David Perlman
(74) *Attorney, Agent, or Firm* — SQUIRE PATTON BOGGS (US) LLP

(57) ABSTRACT

Systems, methods, apparatuses, and computer program products for contactless image-based blood oxygen estimation. A method may include receiving an image or video of a part of a subject captured by a camera of a computing device. The method may also include extracting a region of interest of the part of the subject from the image or video. The method may further include performing feature extraction of the region of interest. In addition, the method may include estimating a blood oxygen saturation level of the subject based on a spatial and temporal data analysis of more than two color channels. Feature extraction and estimation of the blood oxygen saturation level may include implementing a combination of spatial averaging, color channel mixing, and temporal trend analysis.

18 Claims, 15 Drawing Sheets

(51) Int. Cl.

| | |
|---|---|
| *G06V 10/56* | (2022.01) |
| *G06V 10/62* | (2022.01) |
| *G06V 10/82* | (2022.01) |
| *G06V 40/10* | (2022.01) |

(52) U.S. Cl.

CPC .............. *G06V 10/62* (2022.01); *G06V 10/82* (2022.01); *G06V 40/11* (2022.01); *G06V 40/117* (2022.01); *G06V 40/15* (2022.01)

(56) References Cited

OTHER PUBLICATIONS

Scully et al.; "Physiological Parameter Monitoring from Optical Recordings With a Mobile Phone;" IEEE Transactions on Biomedical Engineering, vol. 59, No. 2; Jul. 29, 2011.

Lu et al.; "A Prototype of Reflection Pulse Oximeter Designed for Mobile Healthcare;" IEEE Journal of Biomedical and Health Informatics, vol. 20, No. 5; Aug. 19, 2015.

Ding et al.; "Measuring Oxygen Saturation With Smartphone Cameras Using Convolutional Neural Networks;" IEEE Journal of Biomedical and Health Informatics, vol. 23, No. 6; Dec. 17, 2018.

Bui et al.; "Smartphone-Based SpO2 Measurement by Exploiting Wavelengths Separation and Chromophore Compensation;" ACM Transactions on Sensor Networks, vol. 16, No. 1, Article 9; Jan. 2020.

Guazzi et al.; "Non-contact measurement of oxygen saturation with an RGB camera;" Biomed Opt Express, vol. 6, No. 9; Aug. 11, 2015.

Sun et al.; "Robust non-contact peripheral oxygenation saturation measurement using smartphone-enabled imaging photoplethysmography;" Biomed Opt Express, vol. 12, No. 3; Mar. 1, 2021.

* cited by examiner

Receive an image or video of a part of a subject captured by a camera of a computing device — 1500

Extract a region of interest of the part of the subject from the image or video — 1505

Perform feature extraction of the region of interest — 1510

Estimate a blood oxygen saturation level of the subject based on a spatial and temporal data analysis of more than two color channels — 1515

CONTACTLESS IMAGE-BASED BLOOD OXYGEN ESTIMATION

CROSS-REFERENCE TO RELATED APPLICATION

This application claims priority to U.S. provisional patent application No. 63/214,641 filed on Jun. 24, 2021. The contents of this earlier filed application are hereby incorporated by reference herein in their entirety.

STATEMENT REGARDING FEDERALLY SPONSORED RESEARCH

This invention was made with government support under ECCS2030430 and ECCS2030502 awarded by the National Science Foundation. The government has certain rights in the invention.

FIELD

Some example embodiments may generally relate to virtual and augmented reality multifocal displays. For example, certain embodiments may relate to apparatuses, systems, and/or methods for contactless image-based blood oxygen estimation.

BACKGROUND

Peripheral blood oxygen saturation ($SpO_2$) shows the ratio of oxygenated hemoglobin to total hemoglobin in the blood, which serves as a vital health signal for the operational functions of organs and tissues. Specifically, $SpO_2$ is an important physiological parameter that represents the level of oxygen supply in the blood, and reflects the adequacy of respiratory function. Thus, the estimation and monitoring of $SpO_2$ are essential for the assessment of lung function and the treatment of chronic pulmonary diseases.

Conventional $SpO_2$ measurement methods rely on contact-based sensing, including fingertip pulse oximetry and its variants in smartwatches and smartphones. The conventional approach of estimating $SpO_2$ via pulse oximeter adopts the ratio-of-ratios (RoR). The RoR principle is based on the different optical absorption rates of the oxygenated hemoglobin ($HbO_2$) and deoxygenated hemoglobin (Hb) at 660 nm (red) and 940 nm (infrared) wavelengths. By illuminating red and infrared lights on the peripheral microvascular bed of tissue such as the fingertip, the intensity of the transmitted light on the receiver end of the pulse oximeter contains pulsatile information to derive the level of blood oxygen saturation. Other ways of measuring $SpO_2$ is blood gas analysis, which is invasive and painful, and requires well-trained healthcare providers to perform the test. In contrast, the pulse oximeter is noninvasive and provides readings in nearly real-time, and is therefore more tolerated and convenient for daily use. However, the pulse oximeter is known to have a deviation of ±2% when the blood oxygen saturation is in the range of 70% to 99%.

Although conventional methods can provide measurements of $SpO_2$, these conventional contact-based methods may cause discomfort and skin irritation, especially for people with sensitive skin, and are not always accessible to the public. However, with the ubiquity of smartphones and the growing market of smart fitness devices, the RoR principle has been applied to new non-clinical settings for $SpO_2$ measurement. These methods require a user to use his/her fingertip to cover an optical sensor, and a nearby light source to capture the reemitted light from the illuminated tissue. As noted above, these $SpO_2$ estimation methods are all contact-based. They may irritate sensitive skin, present risks of cross contamination, or cause a sense of burning from the heat built up if the fingertip is in contact with the flashlight on for an extended period of time. Thus, there is a need to provide a way to measure $SpO_2$ by means of contactless techniques, which ahs the potential to be adopted in health screening and telehealth.

SUMMARY

Some example embodiments may be directed to a method. The method may include receiving an image or video of a part of a subject captured by a camera of a computing device. The method may also include extracting a region of interest of the part of the subject from the image or video. The method may further include performing feature extraction of the region of interest. In addition, the method may include estimating a blood oxygen saturation level of the subject based on a spatial and temporal data analysis of more than two color channels. In certain embodiments, feature extraction and estimation of the blood oxygen saturation level may include implementing a combination of spatial averaging, color channel mixing, and temporal trend analysis.

Other example embodiments may be directed to an apparatus. The apparatus may include at least one processor and at least one memory including computer program code. The at least one memory and computer program code may be configured to, with the at least one processor, cause the apparatus at least to receive an image or video of a part of a subject captured by a camera of a computing device. The apparatus may also be caused to extract a region of interest of the part of the subject from the image or video. The apparatus may further be caused to perform feature extraction of the region of interest. In addition, the apparatus may be caused to estimate a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

Other example embodiments may be directed to an apparatus. The apparatus may include means for receiving an image or video of a part of a subject captured by a camera of a computing device. The apparatus may also include means for extracting a region of interest of the part of the subject from the image or video. The apparatus may further include means for performing feature extraction of the region of interest. In addition, the apparatus may include means for estimating a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

In accordance with other example embodiments, a non-transitory computer-readable medium may be encoded with instructions that may, when executed in one or more machines or one or more hardware devices, perform a method. The method may include receiving an image or video of a part of a subject captured by a camera of a computing device. The method may also include extracting a region of interest of the part of the subject from the image or video. The method may further include performing feature extraction of the region of interest. In addition, the method may include estimating a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

Other example embodiments may be directed to a computer program product that performs a method. The method may include receiving an image or video of a part of a subject captured by a camera of a computing device. The method may also include extracting a region of interest of the part of the subject from the image or video. The method may further include performing feature extraction of the region of interest. In addition, the method may include estimating a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

BRIEF DESCRIPTION OF THE DRAWINGS

For a proper understanding of example embodiments, reference should be made to the accompanying drawings, wherein:

FIG. 1($b$) illustrates an example system for SpO$_2$ prediction, according to certain embodiments.

FIG. 2($b$) illustrates another example of heart rate estimation, according to certain embodiments.

FIG. 6($b$) illustrates another bar plot of the SVR/PU case, according to certain embodiments.

FIG. 11($b$) illustrates a histogram of SpO$_2$ value sin a collected dataset, according to certain embodiments.

FIG. 12($b$) illustrates training vs. validation predictions, according to certain embodiments.

FIG. 13($b$) illustrates boxplots comparing additional distributions of correlations, according to certain embodiments.

DETAILED DESCRIPTION

Figure 1A:
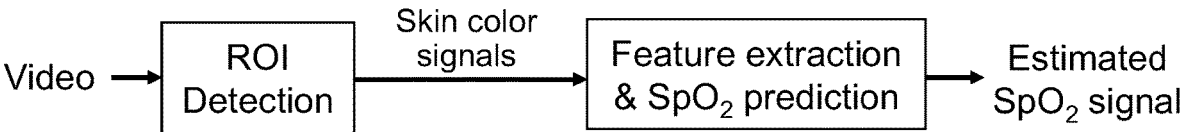
FIG. 1($a$) illustrates an example system for SpO$_2$ estimation, according to certain embodiments.

It will be readily understood that the components of certain example embodiments, as generally described and illustrated in the figures herein, may be arranged and designed in a wide variety of different configurations. The following is a detailed description of some example embodiments of systems, methods, apparatuses, and computer program products for contactless image-based blood oxygen estimation.

The features, structures, or characteristics of example embodiments described throughout this specification may be combined in any suitable manner in one or more example embodiments. For example, the usage of the phrases "certain embodiments," "an example embodiment," "some embodiments," or other similar language, throughout this specification refers to the fact that a particular feature, structure, or characteristic described in connection with an embodiment may be included in at least one embodiment. Thus, appearances of the phrases "in certain embodiments," "an example embodiment," "in some embodiments," "in other embodiments," or other similar language, throughout this specification do not necessarily refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain embodiments, and not in limitation thereof.

Certain embodiments described herein may take advantage of contact-free sensing from a regular RGB camera as well as the conventional SpO$_2$ sensing mechanism from pulse oximeters. For instance, certain embodiments may provide a strategic use of video data of skin regions of interests (ROIs) by performing spatial and temporal data analysis of more than two color channels. Additionally, feature extraction and SpO$_2$ estimation of the certain embodiments may include a combination of spatial averaging of multiple pixels in the region of interest, color channel mixing, and analyzing the temporal trend. It may also be possible to take advantage of both biophysical imaging principles and the availability of participants' video and SpO$_2$ data to learn and determine the details for obtaining SpO$_2$-relevant features and making SpO$_2$ estimation. Under such an synergistic framework, some of the embodiments may determine the specific features and the related detailed parameters explicitly from the biophysical imaging principles, while other embodiments use these principles to guide a neural network to learn ways to combining the input video signals and determining the corresponding parameters for making the estimation. These latter embodiments may "learn" the specific SpO$_2$-relevant features to extract and carry out feature extraction and SpO$_2$ estimation in a holistic manner.

Figure 9:
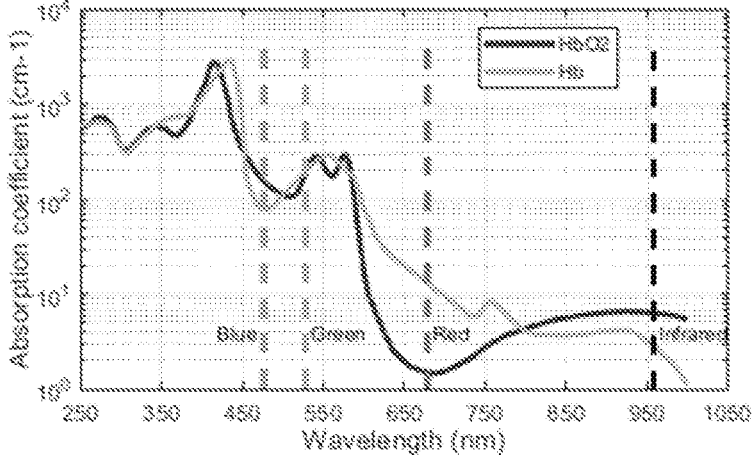
FIG. 9 illustrates an example of extinction coefficient curves of hemoglobin, according to certain embodiments.

The pulse oximeter, designed by the RoR principle, may leverage the optical absorbance difference of Hb and HbO$_2$ at two wavelengths, at the red and infrared wavelengths as illustrated in FIG. 9. As illustrated in FIG. 9, the difference between oxygenated hemoglobin (HbO$_2$) and deoxygenated hemoglobin (Hb) means that these channels contain useful information for SpO$_2$ prediction by means of optophysiological principles. For the commonly seen pulse oximeters, lights at the red and infrared wavelengths are emitted and attenuated by the blood and tissue, and received by an optical sensor, conveying information about pulsatile blood volume. The pulsatile blood volumes at the two wavelengths are further processed to obtain an SpO$_2$ estimate.

Based on the traditional RoR principle used to design the pulse oximetry, many contactless methods are developed with a similar spirit that may utilize two color channels of videos in lieu of traditional narrowband red and infrared wavelengths. Based on the setup of cameras and light sources, existing noncontact, video-based SpO$_2$ estimation methods can be grouped into two categories. Methods from the first category may utilize monochromatic sensing similar to conventional pulse oximetry. They may use either high-end monochromatic cameras with selected optical filters or controlled monochromatic light sources. The other category may use consumer-grade RGB cameras, such as digital webcams. All these video-based non-contact SpO$_2$ estimation methods may utilize the difference in the optophysiological characteristics of oxygenated hemoglobin and deoxygenated hemoglobin. The monochromatic light sources and sensors may be selected to have accurate control of the absorption effect of hemoglobin, while the consumer-grade digital cameras, including webcams and smartphone cameras, may have a wider sensing band and are more challenging for SpO$_2$ sensing.

As described above, certain embodiments may implement the RoR model for SpO$_2$ measurement. For instance, a light source with spectral distribution $I(\lambda)$ illuminating the skin may be considered, and a remote color camera with spectral responsivity $r(\lambda)$ recording a video may be considered. The light from the source may travel through the tissue, and part of the light in the tissue may be reemitted to be received by the color camera. During each cardiac cycle, the heart muscle contracts and relaxes, so that the blood is pumped in the body and travels back to the heart. During this process, the blood volume increases and decreases in the arterial vessels, causing increased and decreased light absorption. According to a skin-reflection model, the color camera may receive the specularly reflected light from the skin surface, and the diffusely reemitted light from the tissue-light interaction that contains the cardiac-related pulsatile information. Based on the verified assumption that the specular reflection components can be ignored if the movement is minimized, the camera sensor response at time t can be expressed as:

$$S_c(t) = \int_{\Theta_c} I(\lambda)*e-\mu d(\lambda,t)*r_c(\lambda)d\lambda. \tag{1}$$

In equation (1), the $\lambda$ is the wavelength, the integral range $\Lambda_c$ captures the responsive wavelength band of channel c of the camera, $I(\lambda)$ is the spectral intensity of the light source, $\mu_d(\lambda, t)$ is the diffusion coefficient, and $r_c(\lambda)$ is the sensor response of channel c of the camera.

According to the Beer-Lambert's law, the diffusion coefficient $\mu_d(\lambda, t)$ can be expanded into:

$$\mu_d(\lambda,t) = \varepsilon_t(\lambda)C_t l_t + [\varepsilon_{Hb}(\lambda)C_{Hb} + \varepsilon_{HbO_2}(\lambda)C_{HbO_2}]l(t), \tag{2}$$

where $\varepsilon_{Hb}, \varepsilon_{HbO_2}$, and $\varepsilon_t$ are the extinction coefficients of arterial deoxyhemoglobin, arterial oxyhemoglobin, and other tissues including the venous blood vessel, respectively; $C_t$, $C_{Hb}$, and $C_{HbO_2}$ are the concentrations of the corresponding substances. Further, $l_t$ is the path length that the light travels in the tissue, and may be assumed to be a time-invariant; l(t) is the path length that the light travels in the arterial blood vessels. Further, l(t) is time-varying because the arteries dilate with increased blood during systole compared to diastole.

The integral range $\Lambda_c$ can be simplified to a single value $\lambda_i$ when the camera is monochromatic, and incoming light may be filtered by a narrowband optical filter, or alternatively, the light source may be a narrowband LED. The response of the camera sensor in (1) may be written as:

$$S_c(t) = I(\lambda_i) \cdot \varepsilon^{-\varepsilon_t(\lambda_i)C_i l_t} \cdot r_c(\lambda_i) \cdot e^{-[\varepsilon_{Hb}(\lambda_i)C_{Hb} + \varepsilon_{HbO_2}]l(t)}, \tag{3}$$

In equation (3), $\Delta l = l_{max} - l_{min}$ denote the difference of the light path of the pulsatile arterial blood between diastole when $l(t) = l_{min}$ and systole when $l(t) = l_{max}$. The log-ratio of the response of the cth channel of the camera sensor during diastole and systole may then be written as:

$$R(\lambda_i) = \log\left(\frac{S_c|_{l(t)=l_{min}}}{S_c|_{l(t)=l_{max}}}\right) \tag{4a}$$

$$= [\varepsilon_{Hb}(\lambda_i)C_{Hb} + \varepsilon_{HbO_2}(\lambda_i)C_{HbO_2}]\Delta l. \tag{4b}$$

For two different wavelengths $\lambda_1$ and $\lambda_2$, the RoR can be defined as:

$$RoR(\lambda_1, \lambda_2) = \frac{R(\lambda_1)}{R(\lambda_2)} = \frac{\varepsilon_{Hb}(\lambda_1)C_{Hb} + \varepsilon_{HbO_2}(\lambda_1)C_{HbO_2}}{\varepsilon_{Hb}(\lambda_2)C_{Hb} + \varepsilon_{HbO_2}(\lambda_2)C_{HbO_2}} \tag{5}$$

Since SpO$_2$=C$_{HbO_2}$/(C$_{HbO_2}$+C$_{Hb}$), the relation between RoR and SpO$_2$ can be written as:

$$SpO_2 = \frac{\varepsilon_{Hb}(\lambda_1) - \varepsilon_{Hb}(\lambda_2) \cdot RoR}{\varepsilon_{Hb}(\lambda_1) - \varepsilon_{HbO_2}(\lambda_1) + [\varepsilon_{HbO_2}(\lambda_2) - \varepsilon_{Hb}(\lambda_2)] \cdot RoR} \tag{6a}$$

$$\approx \alpha \cdot RoR + \beta \tag{6b}$$

In equations (6a) and (6b), the linear approximation may be obtained by a Taylor expansion.

The linear RoR model in (6b) may be applied under different SpO$_2$ measurement scenarios. For instance, for pulse oximeters, $\lambda_1 = 660$ nm and $\lambda_2 = 940$ nm may be used to leverage the optical absorption difference of Hb and HbO$_2$ at the two wavelengths. In other embodiments, when using narrowband light sources or monochromatic camera sensors for contactless SpO$_2$ monitoring, different combinations of ($\lambda_1$, $\lambda_2$) may be explored. Further, when using consumer-grade RGB cameras two out of the three available RGB channels may be used for the linear RoR model.

Among the above-mentioned SpO$_2$ estimation methods using consumer-grade RGB cameras, the SpO$_2$ data collected may cover a small dynamic range (mostly above 95%), which may not be very meaningful. However, a fitted linear relation between RoR and SpO$_2$ may be achieved for data that last several minutes. These limitations can be attributed to that, unlike the signals captured in the narrowband setting that is modeled precisely by (3) and (4), all three RGB color channels capture a wide range of wavelengths from the ambient light, as is described in equation (1). The aggregation of the broad range of wavelengths lowers the optical difference between Hb and $HbO_2$, and makes it less optically selective than narrowband sensors used in oximeters. Thus, to address this issue, certain embodiments may disentangle the aggregation through a combination of the pulsatile signals from all three channels of RGB videos to efficiently distill the $SpO_2$ information.

In certain embodiments, a multi-channel RoR method may be used for non-contact $SpO_2$ monitoring using hand videos captured by cameras including, for example, smartphone cameras under ambient light. For instance, certain embodiments may exploit all three RGB channels to extract features for $SpO_2$ prediction, instead of being limited to two wavelengths/color channels as in traditional RoR methods. Certain embodiments may also take into consideration the underlying optophysiological model given the smartphone camera as the remote sensor and the ambient light environment. In other embodiments, the multi-channel RoR based method may achieve a mean absolute error of 1.26% in $SpO_2$ estimation with the pulse oximeter as the reference, which is 25% lower than that of the traditional RoR model.

According to certain embodiments, the RGB signals may be filtered with a narrow adaptive bandpass (ABP) filter centered at an accurately estimated heart rate (HR) to obtain the most relevant cardiovascular-related AC component from each color channel for feature extraction. Certain embodiments may also systematically analyze and verify the important roles of both the narrow ABP filter and the accurate HR tracking for accurate $SpO_2$ monitoring.

According to other example embodiments, data collection may be accomplished by using the hand as the signal source instead of an individual's face. In doing so, it may be advantageous at least because there is less of a concern for privacy, and potentially being more tolerant to different skin tones than the face. Certain embodiments further analyze the impact of the sides of the hand and skin tones on the $SpO_2$ estimation performance. Given the collected dataset of certain embodiments, it has been found that using the palm side for video capturing has a good $SpO_2$ estimation performance regardless of the skin tones. There are also no significant performance differences between skin-tone subgroups if the palm side is used for video capturing.

As described herein, some neural network work for $SpO_2$ prediction may explore prediction, but not the model explainability. Explainability/interpretability may be highly desirable in many applications yet often not sufficiently addressed, partly due to the black box nature of neural networks. From a healthcare standpoint, explainability is a key factor which should be taken into account at the beginning of the design of a system. To extract features from the skin color signals and estimate $SpO_2$, certain embodiments provide physiologically motivated neural network structures. These structures may be designed to be physically explainable. For heart rate sensing and respiratory rate sensing, the RGB skin color signals may be combined first, as in the plane-orthogonal-to-skin (POS) algorithm, followed by temporal feature extraction. In contrast, for $SpO_2$ sensing methods such as the RoR, the color components are combined at the end. The neural network structures of certain embodiments explore different arrangements of channel combination and temporal feature extraction. As such, certain embodiments may systematically compare the performance of explainable model structures.

Figure 1B:
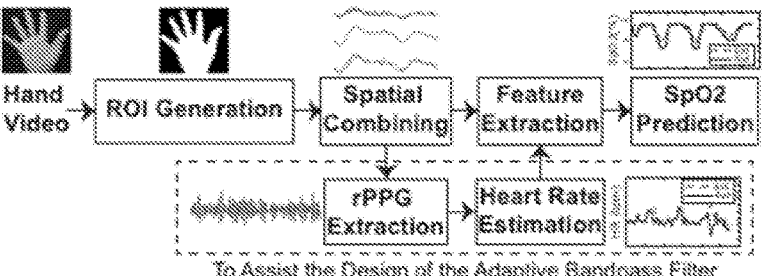

FIG. 1(a) illustrates an example system for $SpO_2$ estimation, according to certain embodiments, and FIG. 1(b) illustrates an example system for $SpO_2$ prediction, according to certain embodiments. In particular, FIG. 1 illustrates an example procedure for the $SpO_2$ estimation from smartphone captured hand videos. According to certain embodiments, the pixels from the hand region may be utilized for prediction, and a remote photoplethysmogram (rPPG) signal may be extracted for heart rate (HR) estimation. Furthermore, multi-channel RoR features may be derived from the spatially combined RGB signals with the help of the HR-guided filters. The extracted features may then be used for $SpO_2$ prediction.

In certain embodiments, first, the hand is detected as the region of interest (ROI) for each frame. Second, the spatial average from the ROI is calculated to obtain three time-varying signals of RGB channels. In some embodiments, the averaged RGB signals may be extracted to estimate HR, and to acquire the filtered cardio-related AC components using an HR-based adaptive bandpass filter. Additionally, the ratio between the AC and the DC components for each color channel, and the pairwise ratios of the resulting three ratios may be computed as the features for a regression model where $SpO_2$ is treated as the label.

As illustrated in FIG. 1, ROI may be generated via thresholding and spatial combining. For instance, to facilitate the data collection with good quality, certain embodiments may use a rectangle to enclose the target hand region. Other embodiments may use an interactive user interface for this step, which can be replaced by an automated hand detection algorithm if desired. Additionally, the pixels in this region may be converted from the RGB color space to the YCbCr color space, and the Cr channel may be used to determine a threshold that best differentiates the skin pixels from the background using the Otsu algorithm. Other embodiments may apply morphological erosion and dilation operations with a median filter to exclude noise pixels outside the region of the binary hand mask. The final hand-shaped mask may be considered as the ROI, and an example is shown in the second picture in FIG. 1. For all n frames in the video, the spatial average values of the red, green, and blue channels in the ROI may be calculated, and denote them as $\bar{r}, \bar{g}, \bar{b} \in \mathbb{R}^{1 \times n}$, and arrange them into a matrix $A = [\bar{r}; \bar{g}; \bar{b}] - \mathbb{R}^{3 \times n}$.

As further illustrated in FIG. 1, the prediction procedure may include rPPG extraction and HR estimation. According to certain embodiments, in a RoR method, after matrix A is calculated, the AC component for each channel of A may be quantified by either the standard deviation or the peak-to-valley amplitude. Since the signal-to-noise ratio (SNR) is lower for the video capture by a smartphone in a contactless manner, certain embodiments may use an adaptive bandpass filter centered at the HR frequency to clean the RGB channel signals to extract the AC components more precisely.

According to certain embodiments, HR can be measured contact-free by capturing the pulse-induced subtle color variations of the skin. The pulse signal (e.g., rPPG), can be obtained from applying the plane-orthogonal-to-skin (POS) algorithm, which defines a plane orthogonal to the skin tone in the RGB space for robust rPPG extraction. The HR may then be tracked from the rPPG signal via an adaptive multi-trace carving (AMTC) algorithm that tracks the HR from the spectrogram of rPPG by dynamic programming and adaptive trace compensation.

9

10

Figure 2A:
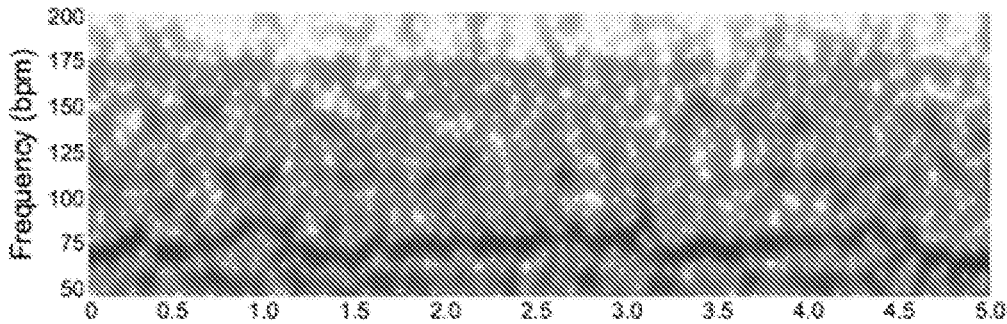
FIG. 2($a$) illustrates an example of heart rate estimation, according to certain embodiments.
Figure 2B:
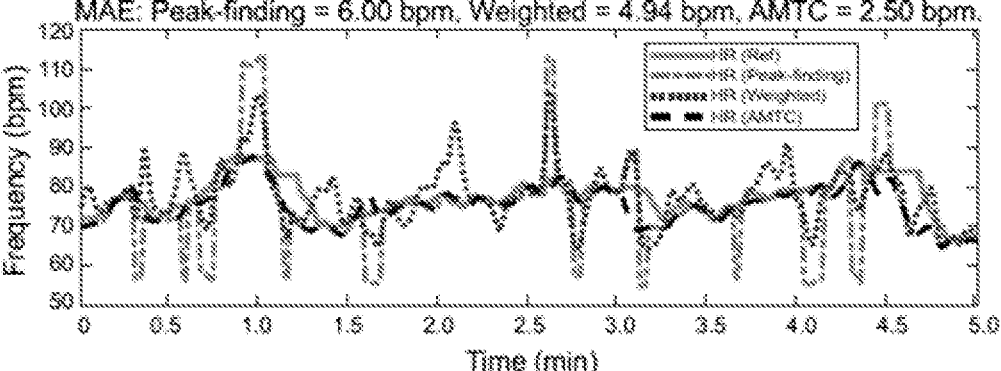

To analyze the role of accurate HR tracking for feature extraction, certain embodiments may implement a peak-finding method and a weighted energy method for frequency estimation to compare with AMTC. The peak-finding method may take the peaks of the squared magnitude of the Fourier transform of rPPG as the estimated HR values. The weighted energy method may find the heart rate by weighing the frequency bins in the corresponding frame of the spectrogram of rPPG. Compared to the peak-finding method, the weighted energy method may be more robust to outliers in frequency. FIGS. 2(a) and 2(b) illustrate an example of the HR estimation results by the peak-finding method, the weighted energy algorithm, and AMTC, respectively, according to certain embodiments. In particular, FIG. 2(a) illustrates a spectrogram of an rPPG signal, according to certain embodiments. Further, FIG. 2(b) illustrates a reference HR signal and HR signals estimated by the peak-finding method, the weighted energy frequency estimation algorithm, and the AMTC algorithm, respectively, according to certain example embodiments. As shown in FIG. 2(b), the mean absolute errors (MAEs) of the HR estimation algorithms are 6.00, 4.94, and 2.50 bpm, respectively.

As further illustrated in FIG. 1, the prediction procedure of SpO$_2$ may include feature extraction. In feature extraction, certain embodiments may use a processing window of 10 seconds with a step size of 1 second to segment the whole video into L windows. Within each window, the DC and AC components of the RGB channels may be calculated to build a feature vector f.

For the DC component, certain embodiments may use a second-order lowpass Butterworth filter with a cutoff frequency at 0.1 Hz. Additionally, the DC component may be estimated using the median of the lowpass filtered signal of each window. As for the AC component, the estimated HR values may be used as the center frequencies for the adaptive bandpass (ABP) filters to extract the AC components of the RGB channels, which eliminates frequency components that are unrelated to the cardiac pulse. Other embodiments may adopt an 8th-order Butterworth bandpass filter with ±0.1 Hz (±0.6 bpm) bandwidth, centering at the estimated HR of the current window. The magnitude of the AC component may be estimated using the average of the peak-to-valley amplitudes of the filtered signals within the current processing window.

In certain embodiments, the normalized AC components may be defined at the ith window as $$R(i, c) = \frac{AC(i, c)}{DC(i, c)},$$

where $c \in \{r, g, b\}$ represents color channel, and $i \in \{1, 2, \ldots, L\}$. Additionally, certain embodiments may define the multi-channel RoR based feature vector of the ith window as $$f_i = \left[ R(i, r), R(i, g), R(i, b), \frac{R(i, r)}{R(i, g)}, \frac{R(i, r)}{R(i, b)}, \frac{R(i, g)}{R(i, b)} \right] \in \mathbb{R}^{1 \times 6}.$$

According to certain embodiments, linear regression (LR) and support vector regression (SVR) may be used to learn the mapping between the features and the SpO$_2$ level. Since LR captures the linear relationship, it has limited learning capability, and may serve as a baseline. The objective function is $$\min_{w} \|y - Fw\|^2 + \lambda \|w\|_2^2,$$

where $y = [\mathcal{Y}_1, \ldots, \mathcal{Y}_L]^T \in \mathbb{R}^{L \times 1}$ contains the target SpO$_2$ values, $F = [f_1; \ldots; f_L] \in \mathbb{R}^{L \times 6}$ is the feature/data matrix derived from the input, and $w \in \mathbb{R}^{6 \times 1}$ contains the weights. In certain embodiments, an $\ell_2$-regularization term is added to the objective function to avoid rank deficiency caused by the collinearity among features. To select the optimal regularization parameter $\lambda$, a 5-fold cross-validation may be used. In addition to LR, certain embodiments may use the SVR to capture the nonlinearity of the features. Additionally, the Libsvm library may be used for training the $\in$-SVR, $$\min_{w,b} \frac{1}{2} \|w\|^2 + C \sum_{k=1}^{L} \mathcal{L}_\in(y_i, w^T \phi(f_i) + b,$$

where $\mathcal{L}_\in$ is the linear $\in$-insensitive loss function. In certain embodiments, the implementation may use the radial basis function (RBF) kernel to capture the nonlinearity. Additionally, the hyperparameters, including the penalty cost C and the kernel parameter $\gamma$ of kernel f unction $K(f_i, f_j) = \phi(f_i)^T \phi(f_j) = \exp(-\gamma \|f_i - f_j\|^2)$ are selected via a grid search over a 5-fold cross-validation loss.

In certain embodiments, once an estimated weight vector $\hat{w}$ is learned from the linear or support vector regression, $\hat{w}$ may then be used to predict a preliminary SpO$_2$ signal. Further, a 10-second moving average window may be applied to smooth out the preliminarily predicted signal to obtain the final predicted SpO$_2$ signal.

Examples of Multi-Channel RoR Based Estimation

Fourteen volunteers, including eight females and six males, were enrolled, with an age range between 21 and 30, and Fitzpatrick skin types II-V. There were two, eight, one, and three participants having skin types II, III, IV, and V, respectively. None of the participants had any known cardiovascular or respiratory diseases. During the data collection, participants were asked to hold their breath to induce a wide dynamic range of SpO$_2$ levels. In some embodiments, the SpO$_2$ range for a healthy person may be from 95% to 100%. By holding their breath, the SpO$_2$ level can drop below 90%. Once the participant resumes normal breathing, the SpO$_2$ will return to the level before the breath-holding.

Figure 3:
FIG. 3 illustrates an experiment setup, according to certain embodiments.
Figures 11A, 11B:
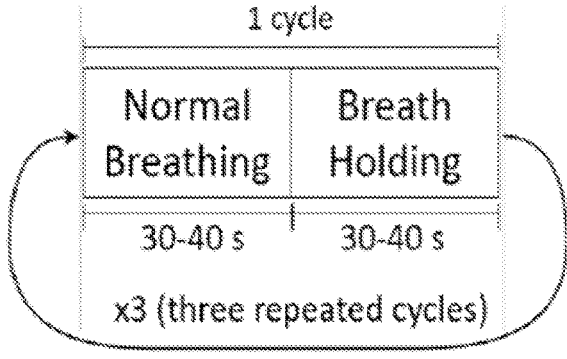
FIG. 11($a$) illustrates an example breathing protocol, according to certain embodiments.

During data collection, each participant was recorded for two sessions. During the recording, the participant sat comfortably in an upright position and put both hands on a clean dark foam sheet placed on a table. FIG. 3 illustrates an experiment setup, according to certain embodiments. In particular, as shown in FIG. 3, the palm side of the right hand and the back side of the left hand were facing the camera. These two hand-video capturing positions are defined as palm up (PU) and palm down (PD), respectively. Simultaneously, a Contec CMS-50E pulse oximeter was clipped to the left index finger to measure the participant's SpO$_2$ level at the sampling rate of 1 Hz. The oximeter may be adopted clinically as to be within a ±2% deviation from the invasive standard for SpO$_2$. Thus, certain embodiments may use the oximeter measurement results as the reference in the experiments. A smartphone camera was used for video recording at the sampling rate of 30 fps, and the video started 30 seconds before the oximeter starts, and stopped immediately after the oximeter ends to allow for proper time synchronization. The participants were asked to hold their breath for 30-40 seconds to lower the SpO$_2$ level, and were told to resume normal breathing for 30-40 seconds if they felt discomfort. The aforementioned process is defined as one breath-holding cycle. In each session, the breath-holding cycles were repeated three times, as illustrated in FIG. 11(a).

After the first session, the participants were asked to relax for at least 15 minutes before attending the second session for data collection. From the data collection protocol using breath-holding, it was possible to obtain the $SpO_2$ measurements with a dynamic range from 89% to 99%. A histogram of $SpO_2$ values in the collected dataset is illustrated in FIG. 11(b).

According to certain embodiments, the total length of recording time for all fourteen participants was 138.9 minutes. The data size was relatively small for large-scale neural network training. The available data, however, was adequate for the principled multi-channel signal based approach to $SpO_2$ monitoring, showing a benefit of combining signal processing and biomedical knowledge and modeling with data than the primarily data-driven approach.

In certain embodiments, when the CMS-50E oximeter was turned on and ready for measurement, the first reading is displayed a few seconds after the finger is inserted. This delay may be due to oximeter's internal firmware startup and algorithmic processing. Since the video and the oximeter readings need to be synchronized using their precise starting time stamps, the delay in the oximeter can introduce misalignment errors in the reference data used to train the regression model. To avoid the misalignment, the delay was first estimated, and then compensated for the delay in the training and testing. To do so, one participant was asked to repeatedly place the left index finger, middle finger, and ring finger into the oximeter 50 times each and obtained the average delay time of 1.8 s, 1.9 s, and 1.7 s, respectively. Since the left index finger is used for reference data collection in the setup, 1.8 s was taken as the delay. To further examine whether there exists any difference among the delays from the three fingers, a one-way ANOVA test was conducted. The p-value was 0.14, which shows no statistically significant different delays among the three fingers.

The performance of the algorithm may be evaluated using the mean absolute error (MAE) (equation (7a)), and Pearson's correlation coefficient $\rho$ (equation (7b)) given below:

$$MAE(y, \hat{y}) = \frac{1}{N} \sum_{i=1}^{N} \|y_i - \hat{y}_i\|, \tag{7a}$$

$$\rho(y, \hat{y}) = \frac{(y - \bar{y})^T (\hat{y} - \bar{\hat{y}})}{\|y - \bar{y}\|_2 \|\hat{y} - \bar{\hat{y}}\|_2}. \tag{7b}$$

In equations (7a) and (7b), $y = [\mathcal{Y}_1, \ldots, \mathcal{Y}_N]^T$, $\hat{y} = [\widehat{\mathcal{Y}_1}, \ldots, \widehat{\mathcal{Y}_N}]^T$, $\bar{y}$, and $\bar{\hat{y}}$ denote the reference $SpO_2$ signal, the estimated $SpO_2$ signal, the average values of all coordinates of vectors y and $\hat{y}$, respectively. Additionally, the correlation metric may be adopted to evaluate how well the trend of the $SpO_2$ signal is tracked.

In certain embodiments, the training data from one participant was used to train the regression model for the prediction of his/her testing session recorded a period of time later. In the aforementioned training and testing procedure the models were specifically learned for each participant.

Figure 4:
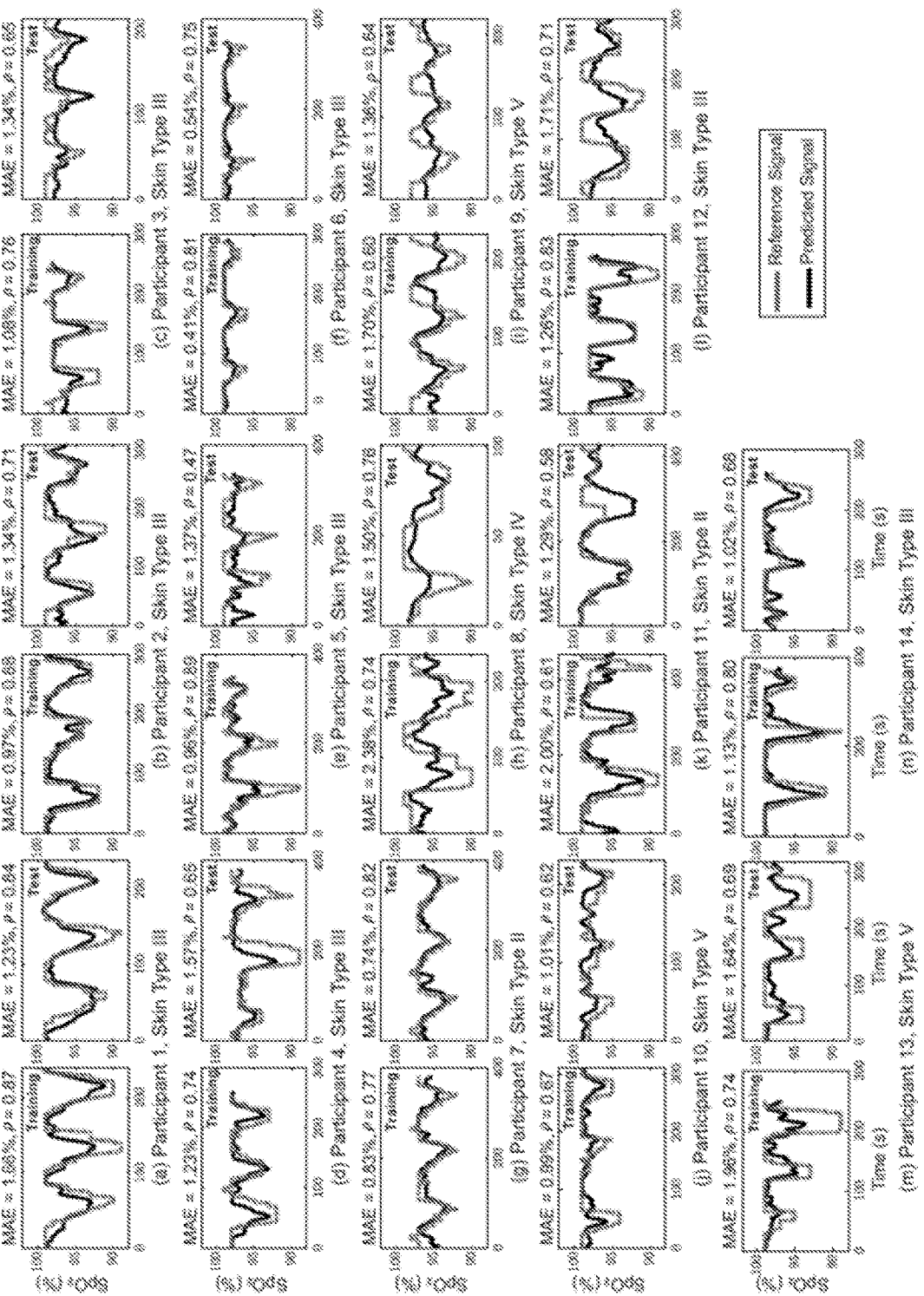
FIG. 4 illustrates learning results of all participants, according to certain embodiments.
Figure 5:
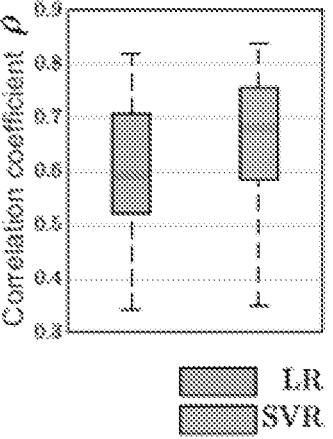
FIG. 5 illustrates distributions contrasting linear and support vector regressions (SVR), according to certain embodiments.

FIG. 4 illustrates learning results of all participants, according to certain embodiments. In particular, FIG. 4 illustrates predicted $SpO_2$ signals for all participants using SVR when the palm is facing the camera (i.e., the palm-up scenario). As illustrated in FIG. 4, the prediction results of training and testing sessions are shown for each participant with reference $SpO_2$ in dash lines, and predicted $SpO_2$ in solid lines. The higher the correlation p and the lower the MAE, the better the predicted $SpO_2$ captures the trend of the reference signal.

In FIG. 4, both training and testing sessions are shown for each participant. The $SpO_2$ curves in each session contain three dips that are a result from breath holding, except for participant #8 who had a shorter session due to limited tolerance of breath-holding. For each participant, the skin-tone information was provided in the subplot, and the accuracy indicators, MAE and p, for $SpO_2$ prediction are shown. In all training sessions, MAE is below 2.4% and p is above 0.6. From this observation, we find that all the predicted $SpO_2$ signals in the training sessions are closely following the reference signals. Furthermore, all testing MAE values are within 1.8%, suggesting that those trained models adapt well to the testing data. While there are a few cycles that the predicted signal does not fully follow the reference signal, such as the second dip for participant #4 and participant #11, the trends are consistent. From experimental summary of the training and testing $SpO_2$ estimation performance of both LR and SVR based methods for both PU and PD cases, it suggests that there may exist a nonlinear relationship between the extracted features and the $SpO_2$ values.

To examine the impact of the side of a hand and the skin tone on the performance of SpO2 estimation, certain example embodiments may examine: (i) whether the side of hand makes a difference in lighter skin (types II and III) or darker skin (types IV and V) or mixed skins (all participants); and (ii) whether the different skin tones matter in PU or PD case.

According to certain embodiments, to study the importance of the feature vector f containing pulsatile information from all RGB channels, the narrow ABP filter, and the passband of ABP filter centered at precise HR frequency tracked by AMTC, three controlled experiments were conducted by removing one factor at a time. The configurations of methods corresponding to the experiments are listed in Table 1 below.

TABLE 1

| Configurations for the ablation study of the pipeline | | | |
|---|---|---|---|
| | Configuration | | |
| Method Index | Multi-channel RoR features? | Narrow ABP filter? | Accurate HR tracking? |
| I | Two-channel RoR | ✓ | ✓ |
| II | ✓ | No ABP | n/a |
| III | ✓ | Wide ABP | ✓ |
| IV | ✓ | ✓ | Peak-finding |
| V | ✓ | ✓ | Weighted energy |
| Proposed | ✓ | ✓ | ✓ |

Figure 6A:
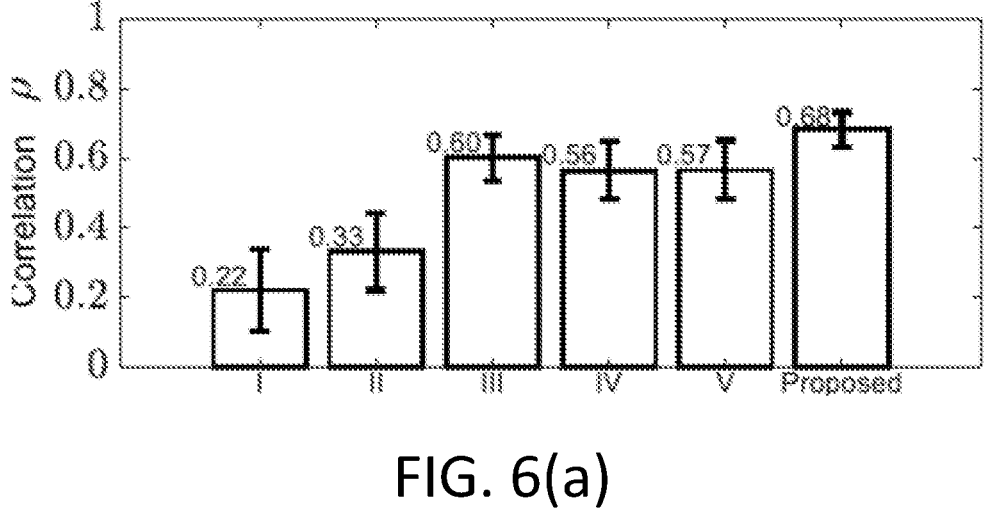
FIG. 6($a$) illustrates a bar plot of the SVR/PU case, according to certain embodiments.
Figure 6B:
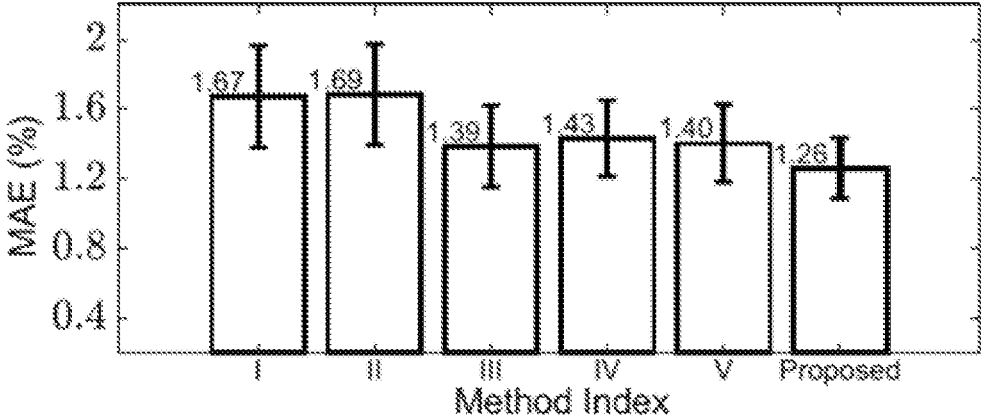

FIG. 6(a) illustrates a bar plot of the SVR/PU case, according to certain embodiments, and FIG. 6(b) illustrates another bar plot of the SVR/PU case, according to certain embodiments. As illustrated in FIGS. 6(a) and 6(b), the height of each bin shows the average of correlation coefficient $\rho$ or the MAE of $SpO_2$ estimation results from testing sessions (SVR, PU case) of all participants. Each pair of error bars corresponds to the 95% confidence interval that is calculated as $\pm 1.966 / \sqrt{N}$, where $\hat{\sigma}$ is the sample standard deviation, and N is the sample size/number of participants. Further, as illustrated in FIGS. 6(a) and 6(b), it can be seen that the larger the correlation, the better; and the smaller the MAE, the better.

Additionally, FIGS. 6(*a*) and 6(*b*) compares the method (method (I)) of RoR with narrow adaptive bandpass filter (nABP) (AMTC) corresponding to the feature extraction method described above. This method includes the nABP centered at AMTC-tracked HR. The only exception is that instead of using the feature vector f that contains multichannel information, only the RoR between the channels as in traditional RoR methods is used. FIGS. 6(*a*) and 6(*b*) also illustrate that the method of certain embodiments (i.e., "proposed") described herein outperforms the method of RoR with nABP by a significant margin. More specifically, the method of certain embodiments improves the correlation coefficient from 0.22 to 0.68, and the MAE from 1.67% to 1.26%. This improvement confirms that the multi-channel feature of certain embodiments help with the more accurate $SpO_2$ monitoring.

The contribution of narrowband ABP filter for feature extraction was also analyzed. Here, two methods were compared to show the necessity of using a narrowband HR-guided bandpass filter. In method (II), feature vector without ABP uses a nonadaptive, generic bandpass filter with the passband over [1, 2] Hz, covering the normal range of HR in secondary mode to replace the HR-based narrow ABP filter. In method (III), the feature vector with wide ABP (AMTC) applied a wider ABP filter with ±0.5 Hz bandwidth than the ±0.1 Hz. This wider ABP filter's center frequency is provided by the AMTC tracking algorithm of the HR described above.

In certain embodiments, the bandpass filters used for methods (II) and (III) have the same bandwidth, 1 Hz. In terms of center frequency, method (II) used a fixed setting at 1.5 Hz, while method (III) was adaptively centered at the estimated HR value. Compared to method (II), method (III) has an improved testing MAE by 18%. Furthermore, compared to method (III), the method of certain embodiments with a narrow ABP filter improves the correlation coefficient $\rho$ for testing by 13% and MAE by 9%, suggesting the contribution of the narrow HR-based ABP filter strategy for AC computation.

The importance of accurate HR tracing on $SpO_2$ monitoring was considered. Specifically, two methods were considered to compare with the method of certain embodiments. In particular, method (IV) involves feature vector with narrow ABP (peak-finding). In method (IV), a narrow ABP filter of bandwidth ±0.1 Hz was applied for extracting the feature vector f. The center frequency of the ABP filter is the HR estimated from the peak-finding algorithm described above. Additionally, in method (V), feature vector with narrow ABP (weighted) may be similar to method (IV), except that the frequency estimation algorithm is replaced by the weighted energy described above.

According to certain embodiments, the averaged MAE of the HR estimation for all participants by the peak-finding algorithm, weighted frequency estimation algorithm, and AMTC algorithm were 7.11 (+3.66) bpm, 6.42 (+3.02) bpm, and 4.14 (+1.72) bpm, respectively.

FIGS. 6(*a*) and 6(*b*) illustrate that methods (IV) and (V) perform similarly with 0.56 vs. 0.57 for correlation p and 1.43% vs. 1.40% for MAE, respectively. Our proposed method guided by the AMTC tracked HR outperforms methods (IV) and (V) by 21% and 19% in correlation, and by 12% and 10% in MAE, respectively. These results suggest that the accurate HR estimation for ABP filter design improves the quality of the AC magnitude by preserving the most cardiac-related signal from RGB channels, which in turn helps with the accurate $SpO_2$ monitoring.

In addition to contact-free $SpO_2$ monitoring, the proposed algorithm of certain embodiments may be evaluated to determine whether it can be applied to a contact-based smartphone setup. To collect data, the left index finger covers the smartphone's illuminating flashlight and the nearby built-in camera, and the camera captures a pulse video at the fingertip. Another smartphone is used to simultaneously record a top view video of the back side of the right hand whose index finger is placed in the oximeter for $SpO_2$ reference data collection. One participant took part in this extended experiment where one training session with three breath-holding cycles was recorded, and three testing sessions were recorded 30 minutes after the training session.

In Table 2, the performance of the proposed algorithm in both the contact-based and contact-free $SpO_2$ measurement settings were compared. The conventional RoR models used were implemented as baseline models for contact-based $SpO_2$ measurement. Additionally, the mean and standard deviation of each window from the red and blue channels were calculated as the DC and AC components. A linear model was built to relate the ratio-of-ratios from the two color channels with $SpO_2$. Further, the median of the pulsatile peak-to-valley amplitude was regarded as the AC component. For the two RoR methods, both LR and SVR were implemented. For contact-free $SpO_2$ measurement, the traditional two-color channel RoR method was taken as the baseline to compare with the proposed method.

TABLE 2

| Comparison of algorithm in both contact and contact-free $SpO_2$ estimation settings | | | | |
|---|---|---|---|---|
| | | Training | | Testing | |
| | | MAE | p | MAE | p |
| Contact | RoR \|10\| (LR) | 1 60% | 0.54 | 1.38% | 0.64 |
| | RoR \|10\| (SVR) | 1.14% | 0.73 | 1.32% | 0.60 |
| | RoR \|11\| (LR) | 1.47% | 0.62 | 1.39% | 0.63 |
| | RoR \|11\| (SVR) | 0.99% | 0.83 | 1.27% | 0.66 |
| | Proposed | 0.91% | 0.84 | 1.17% | 0.81 |
| Contact-free | RoR (2-channel) | 1.61% | 0.73 | 1.75% | 0.36 |
| | Proposed | 1.36% | 0.62 | 1.29% | 0.68 |

Additionally, Table 2 reveals that the proposed algorithm outperforms other conventional RoR models in the contact-based $SpO_2$ monitoring. Even in the contact-free case, the proposed algorithm presents a comparable performance to that of the contact-based cases, despite that the SNR of the fingertip video is better than the SNR from a remote hand video.

Figure 7:
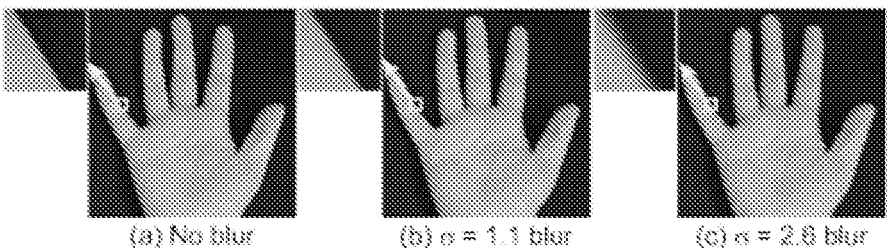
FIG. 7 illustrates an example blurring effect, according to certain embodiments.

Further, it was found that the proposed algorithm demonstrated resilience against blurring. For instance, in the setup described above, the hands were placed on a stable table with a cellphone camera acquiring the skin color of both hands. Ideal laboratory conditions are often not satisfied under practical scenarios, and the hand images captured by the cellphone cameras may be blurred due to being out of focus. The point spread function is modeled as a 2D homogeneous Gaussian kernel. The finite support of the kernel is defined manually to generate perceptually different blurry effects and then the standard deviation $\sigma$ is computed based on the given support. To test different blurry effects, experiments were conducted with two different blurry levels $\sigma=1.1$ (5×5 pixels) and $\sigma=2.6$ (15×15 pixels), respectively. The blurring effects are demonstrated in FIG. 7, which illustrates blurring effects using different blurry level $\sigma$ on hand videos according to certain embodiments. The wider the kernel was, the blurrier the videos were.

Table 3 presents the SVR generated results for PU cases with different σ and kernel sizes. The SVR, PU scenario was used to showcase here as it achieves the best SpO₂ prediction performance, which is verified in the examples described above. From Table 5, it can be seen that the algorithm of certain embodiments is robust to the Gaussian blurring effect. After the σ=1.1 blurring, the testing ρ remains the same, and testing MAE is 6.3% higher than the no blurring case. Additionally, after the σ=2.6 blurring, the testing ρ is 1.5% lower and MAE is 4.0% higher than the no blurring case.

TABLE 3

| | SVR generated results | | | |
| --- | --- | --- | --- | --- |
| | Training | | Testing | |
| | MAE | p | MAE | p |
| σ = 2.6 blur | 141% | 0.72 | 1.31% | 0.67 |
| (15 × 15 pixels) | (±0.50%) | (±0.11) | (±0.35%) | (±0.09) |
| σ = 1.1 blur | 1.42% | 0.70 | 1.34% | 0.68 |
| (5 × 5 pixels) | (±0.59%) | (±0.16) | (±041%) | (±0.10) |
| No blur | 1.33% | 0.76 | 1.26% | 0.68 |
| | (±0.54%) | (±0.09) | (±0.33%) | (±0.10) |

From the recordings of the data collection protocol for voluntary breath-holding, it was observed that HR and SpO₂ are correlated for many participants. That is, in one breath-holding cycle, when the participant starts to hold breath, his/her HR increases and SpO₂ drops as the oxygen runs out. As he/she resumes normal breathing, his/her HR and SpO₂ recovers to be within the normal range. Due to individuals' different physical conditions, in some participants, the peak of the HR signal and valley of the SpO₂ signal happen in such a short time interval that HR and SpO₂ are significantly negatively correlated. This observation is in line with the biological literature where it has been found that breath-holding exercises yield significant changes in the cardiovascular system. In the central circulation, they caused significant changes in heart rate, and in the peripheral circulation, they caused significant changes in arterial blood flow and oxygen saturation.

Figure 8:
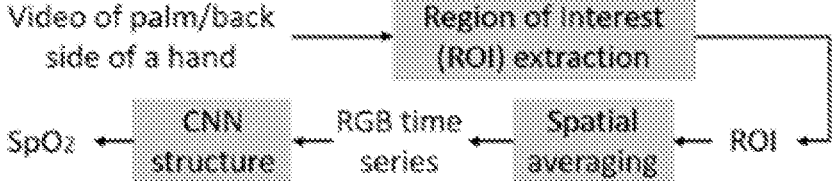
FIG. 8 illustrates an example SpO$_2$ estimation method, according to certain embodiments.

According to other embodiments, convolutional neural networks (CNN) maybe utilized for contactless SpO₂ monitoring from videos captured by cameras including, for example, mobile device cameras (e.g., smartphones). FIG. 8 illustrates an example SpO₂ estimation method, according to certain embodiments. First, the ROI, including the palm and back side of the hand, is extracted from the smartphone captured videos. Second, the ROI is spatially averaged to produce R, G, and B time series. Third, the three time series are fed into an optophysiology-inspired CNN to implicitly learn the features for SpO₂ estimation. Certain embodiments described herein may use neural networks to address the problem of contactless SpO₂ sensing using consumer-grade RGB cameras.

According to certain embodiments may utilize deep learning aided camera-based physiological monitoring. Deep learning has demonstrated promising performance in camera-based physiological measurements, such as HR and breathing rate. An end-to-end convolutional attention network may estimate the blood volume pulse from face videos. Further, frequency analysis may be conducted on the estimated pulse signal for HR and breathing rate tracking. Thus, HR may be directly inferred using a convolutional network with spatial-temporal representation of the race videos as its input.

For instance, certain embodiments may estimate SpO₂ levels using a hand video by leveraging the fact that the color of the skin changes subtly when red cells in the blood carry/release oxygen. In certain embodiments, three-color time series may be extracted by spatial averaging from the skin area of the hand video. The extracted time series may then be fed to optophysiology-inspired neural networks designed to implicitly learn the features by color channel mixing and temporal trend analysis to achieve better and more explainable SpO₂ predictions.

In certain embodiments, the skin color signals may be split up into 10-second segments using a sliding window with a step size/stride of 0.2 seconds to serve as the inputs for neural networks. From an optophysiological perspective, the reflected/reemitted light from the skin for the duration of one cycle of heartbeat (i.e., 0.5-1 seconds for a heart rate of 60-120 bpm) should contain almost the complete information necessary to estimate the instantaneous SpO₂. In certain embodiments, longer segments may be used to add resilience against sensing noise. Since the segment length is one order of magnitude longer than the minimally required length to contain the SpO₂ information, a fully-connected or convolutional structure may be used to adequately capture the temporal dependencies without resorting to a recurrent neural network structure.

Some neural network work for SpO₂ prediction may explore prediction, but not the model explainability. Explainability/interpretability may be highly desirable in many applications yet often not sufficiently addressed, partly due to the black box nature of neural networks. From a healthcare standpoint, explainability is a key factor which should be taken into account at the beginning of the design of a system. To extract features from the skin color signals and estimate SpO₂, certain embodiments provide three physiologically motivated neural network structures. These structures are inspired by domain knowledge-driven physiological sensing methods, and designed to be physically explainable. For heart rate sensing and respiratory rate sensing, the RGB skin color signals may be combined first, as in the plane-orthogonal-to-skin (POS) algorithm, followed by temporal feature extraction. In contrast, for SpO₂ sensing methods such as the RoR, the color components are combined at the end. The neural network structures of certain embodiments explore different arrangements of channel combination and temporal feature extraction. As such, certain embodiments may systematically compare the performance of explainable model structures.

Figure 10:
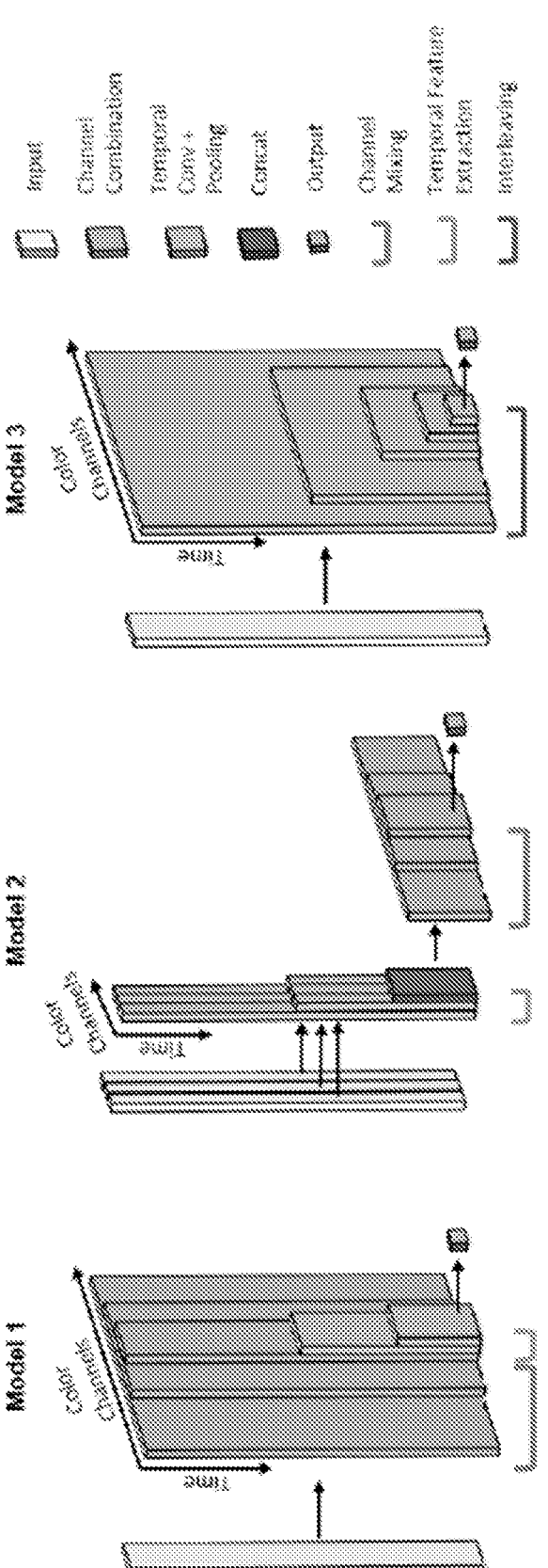
FIG. 10 illustrates an example network structure for predicting an SpO$_2$, according to certain embodiments.

In certain embodiments, channel mixing may be followed by feature extraction. FIG. 10 illustrates an example network structure for predicting an SpO₂, according to certain embodiments. In Model 1, shown as the leftmost structure depicted in FIG. 10, the color channels are combined first using several channel combination layers, and then the resulting features are further processed by temporal convolutional and max pooling to extract the temporal information. A channel combination layer first linearly combines the $C_{in}$ input channels/vectors into $C_{out}$ activation vectors, and then applies a rectified linear unit (ReLU) activation function to obtain the output channels/vectors. Mathematically, the channel combination layer is described as follows:

$$V = \sigma(WU + b\mathbb{1}^T), \quad (8)$$

where $U \in \mathbb{R}^{C_{in} \times L}$ is the input comprised of $C_{in}$ time series/vectors of length L. The initial channel combination layer has an input of three channels with 300 points along the time axis. $W \in \mathbb{R}^{C_{out} \times C_{in}}$ is a weight matrix, where each of the $C_{out}$ rows of the matrix is a different linear combination for the input channels. A bias vector $b \in \mathbb{R}^{C_{out}}$ contains the bias terms for each of the $C_{out}$ output channels, which ensures that each data points in the artificially created segment of length L has the same intercept. $\mathbb{1}^T \in \mathbb{R}^{1 \times L}$ is a row vector of all ones. The nonlinear ReLU function $\sigma(x)=\max(0, x)$ is applied elementwise to the activation map/matrix. The output of the channel combination layer $V \in \mathbb{R}^{C_{out} \times L}$ contains $C_{out}$ channels of nonlinearly combined input channels.

As further shown in Model 1, the channel mixing section concatenates multiple channel combination layers with decreasing channel counts to provide significant nonlinearity. The output of the last channel combination layer has seven channels. After the channel mixing, for temporal feature extraction, multiple convolutional and max pooling layers may be utilized with a downsampling factor of two to extract the temporal features of the channel-mixed signals. When there are multiple filters in the convolutional layer, then there may also be some additional channel combining with each filter outputting a channel-mixed signal. Finally, a single node may be used to represent the predicted SpO$_2$ level.

According to certain embodiments, feature extraction may be followed by channel mixing. In Model 2, the middle structure depicted in FIG. 10, the order of channel mixing and temporal feature extraction is reversed from that in Model 1. The three color channels are separately fed for temporal feature extraction. Additionally, the convolutional layers learn different features unique to each channel. At the output of the temporal feature extraction section, each color channel has been downsampled to retain only the important temporal information. The color channels are then mixed together in the same way as described for Model 1 before outputting the SpO$_2$ value.

In certain embodiments, the feature extraction and channel mixing may be interleaved. As illustrated in FIG. 10, in Model 3, the possibility of interleaving the color channel mixing and temporal feature extraction steps may be explored. As illustrated by the rightmost structure illustrated in FIG. 10, the input is first put through a convolutional layer with many filters and then passed to max pooling layers, resulting in feature extraction along the time as well channel combinations through each filter. The number of filters is reduced with each successive convolutional layer, gradually decreasing the number of combined channels and downsampling the signal in the time domain.

According to certain embodiments, the root-mean-squared-error (RMSE) may be used as the loss function for all models. During training, the model instance at the epoch may be saved with the lowest validation loss. The neural network inputs may be scaled to have zero mean and unit variance to improve the numerical stability of the learning. Additionally, the parameters and hyperparameters of each model structure were tuned using a HyperBand algorithm, which allows for faster and more efficient search over a large parameter space than grid search or random search. It does this by running random parameter configurations on a specific schedule of iterations per configuration, and uses earlier results to select candidates for longer runs. The parameters that were tuned include the learning rate, the number of filters and kernel size for convolutional layers, the number of nodes, the dropout probability, and whether to do batch normalization after each convolutional layer.

Examples of SpO$_2$ Estimation Synergy of Principled Mechanisms and Neural Networks The models of certain embodiments were evaluated on a self-collected dataset. The dataset consisted of hand video recordings and SpO$_2$ data from 14 participants, of which there were six males and eight females between the ages of 21 and 30. Participants were asked to categorize their skin tone based on the Fitzpatrick skin types. The distribution of the participants' skin types is as follows: two participants of type II; eight participants of type III; one participant of type IV; and three participants of type V.

The self-collected dataset may include hand video recordings and SpO$_2$ data from fourteen participants, of which there were six males and eight females between the ages of 21 and 30. Participants were asked to categorize their skin tone based on the Fitzpatrick sin types. The Fitzpatrick skin types classify the skin by its reaction to exposure to sunlight and pigmentation. From type I to type VI, the skin color becomes darker and less prone to be burned by the sunlight. Among the fourteen participants, two are from type II, eight are from type III, one is from type IV, and three are from type V.

Table 4 illustrates a comparison of correlations for lighter vs. darker skin types vs. all skin types in both PU and PD cases, according to certain embodiments. Specifically, Table 4 illustrates a supplement to FIG. 7 with numerical values specified for the factor analysis, including the skin type and the side of the hand. This table presents a comparison of the test correlations from all the three proposed models in palm up (PU) and palm down (PD) data collection modes of lighter skin participants (types II and III), darker skin participants (types IV and V), and all participants. The following may be analyzed in view of Table 4: (i) Whether the different skin types matter in PU or PD case, and (ii) whether the side of the hand matters in lighter skin or darker skin.

TABLE 4

| Comparison of correlations for lighter vs. darker skin types vs. all skin types in both PU and PD cases. | | | | | | |
|---|---|---|---|---|---|---|
| | Lighter | | Darker | | Overall | |
| Hand Mode | Median | IQR | Median | IQR | Median | IQR |
| | Participant-Specific | | | | | |
| PD | 0.44 | 0.50 | 0.48 | 0.20 | 0.45 | 0.41 |
| PU | 0.41 | 0.30 | 0.45 | 0.38 | 0.41 | 0.33 |
| | Leave-One-Participant-Out | | | | | |
| PD | 0.14 | 0.41 | 0.43 | 0.19 | 0.24 | 0.39 |
| PU | 0.35 | 0.46 | 0.31 | 0.31 | 0.34 | 0.42 |

According to certain embodiments, the top panel of Table 5 may be used to examine the participant-specific case. In the PD case, the darker skin group outperforms the light group since the former has a larger median of 0.48 and a smaller IQR of 0.20. In the PU case, the medians of the lighter skin group and darker skin group are 0.41 and 0.45, with IQR being 0.30 and 0.38, respectively. Even though the median from the darker group is 9.8% higher, the IQR is 26.7% worse. Thus, no significant performance difference was observed in the PU case. Additionally, the bottom panel of Table 4 to analyze the results from the leave-one-partici-pant-out experiment. It was observed that in the PD case, the darker skin group with a median of 0.43 outperforms the lighter skin group with a median of 0.14, whereas in the PU case, the performances are comparable. This observation is consistent with the participant-specific experiments that when using the palm as the ROI, the skin color is not a factor to the accuracy of $SpO_2$ estimation.

Certain embodiments may focus on the participant-specific case in the top panel of Table 4. It was found that there is no significant difference between PU and PD cases in our current lighter skin and overall groups, whereas in the darker skin group, the PD case is better than the PU case. Then, focus was placed on the results under the leave-one-participant-out setup in the bottom panel of Table 4. For the darker skin group, the PD case outperforms the PU case, which is consistent with the results from the participant-specific experiments. In contrast, in both the lighter skin group and the mixed group, the PU cases significantly outperform the PD cases.

The reference $SpO_2$ signal was interpolated to 5 sample points per second to match the segment sampling rate using a smooth spline approximation. Each RGB segment and $SpO_2$ value pair was fed into the models as a single data point, and the models output a single $SpO_2$ estimate per segment. To evaluate a model on a recording, the model was sequentially fed all RGB segments from the recording to generate a time series of preliminarily predicted $SpO_2$ values. All predictions greater than 100% $SpO_2$ were clipped to 100% since they are physiologically impossible. Additionally, a 10-second long moving average filter was applied to generate a refined time series of predicted $SpO_2$ values.

Figure 12A:
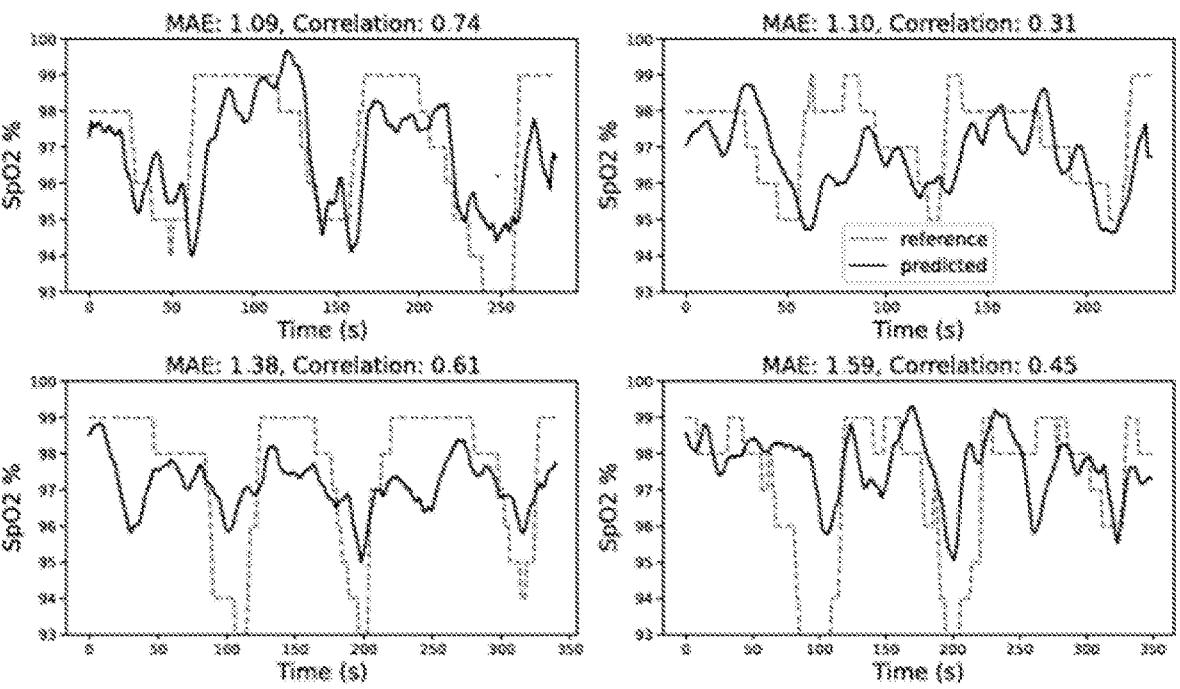
FIG. 12($a$) illustrates test predictions of varying performance with reference SpO$_2$, according to certain embodiments.
Figure 12B:
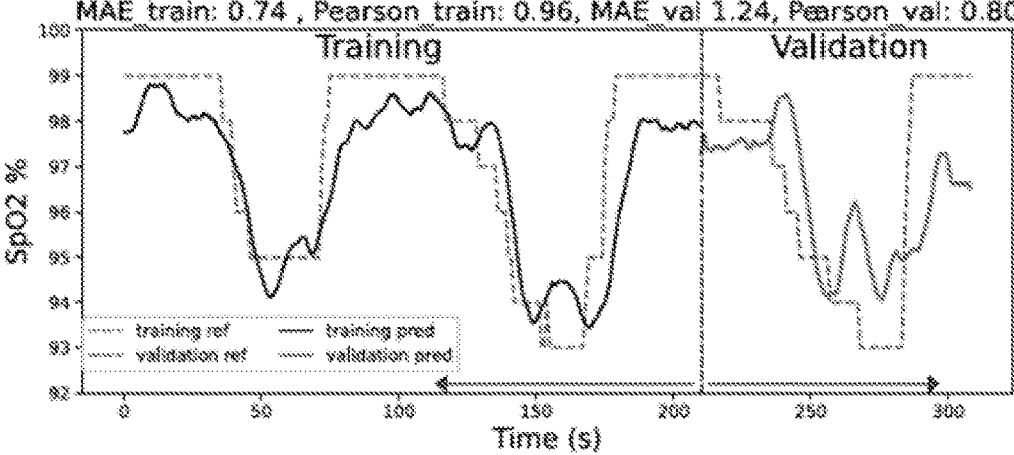

To investigate how well the models could learn to estimate a specific individual's $SpO_2$ from his/her own data, participant-specific experiments were conducted. That is, individualized models were learned for each participant. For instance, Two recordings per participant were captured with at least 15 minutes in between. One recording was used for training and validation of the model and the remaining recording was for testing. An example of the training and validation predictions curves are illustrated in FIG. 12(a). Each recording contains three breathing cycles, and for each training/validation recording, the first two breathing cycles were taken for training and the third cycle is used for validation. Splitting the recordings into cycles instead of randomly sampling the 10-sec overlapping RGB segments ensured that there are no overlapping segments of data between the training and validation set. Example test prediction curves and their correlation and MAE are illustrated in FIG. 12(b). It should be noted that if the correlation is low (e.g., a constant temporal estimate), then the MAE and RMSE metrics are less meaningful. For the participant-specific experiments, due to the small dataset size, the training and validation data were augmented by sampling with replacement. The oversampling also helps address the imbalance in $SpO_2$ data values that is shown in FIG. 11(b).

In each experiment, the model structure and hyper-parameters are first tuned using the training and validation data. Once the model has been tuned, multiple instances of the model were trained using the best-tuned hyper-parameters. Between each instance, the random seed used for model weights initialization and random oversampling were varied. Each model instance was evaluated on the training/validation recording, and the model instance that achieved the highest validation RMSE was selected for evaluation on the test recording. This model was then evaluated on the test recording to obtain the final test result.

Performance comparison of the models of certain embodiments with an existing model reveals that Model 2 was the best in terms of correlation in both PD and PU cases, whereas Model 3 achieved the best in MAE and RMSE, showing that Model 2 and Model 3 are comparably the best in the individualized learning. All of the model configurations of certain embodiments described herein outperformed the existing model. It is worth noting that the international standard for clinically acceptable pulse oximeters tolerates an error of 4%, and the estimation errors were all within this range.

Figure 13A:
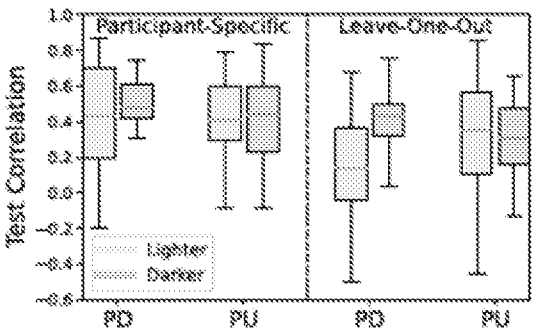
FIG. 13($a$) illustrates boxplots comparing distributions of correlations, according to certain embodiments.
Figure 13B:
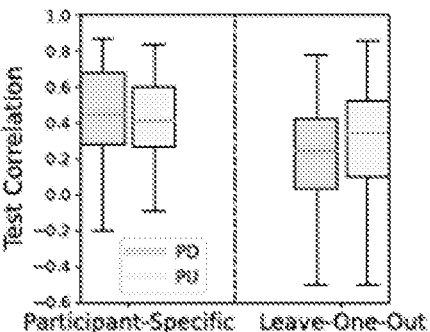

There were two factors, including the skin type and the side of the hand, that may influence the performance of $SpO_2$ estimation. Thus, the following were analyzed: (1) whether the different skin types matter in PU or PD case; and (2) whether the side of hand matters in lighter skin (types II+III) or darker skin (types IV+V). The box plots in FIGS. 13(a) and 13(b) illustrate the distributions of the test correlations from all three models in PU and PD modes of lighter skin and darker skin participants (FIG. 13(a)), and all participants (FIG. 13(b)).

Certain embodiments focused on the left panel of FIG. 14(a). Overall, the medians of darker skin group were larger than those of the lighter skin group. Zooming into the PD case, it can be confirmed that the darker skin group indeed outperformed the light group since the former has a smaller interquartile range (IQR). However, for the PU case, there was no significant performance difference observed, because while the dark skin group was better in a larger median, the light skin group was better in a narrower IQR. As to the left panel of FIG. 13(b), no significant performance difference was observed between PD and PU given one had a better median and the other has a better IQR, when participants of all skin colors were considered together. However, looking at the subset of darker skin group as shown in the left panel of FIG. 11(a), it can be observed that PD was better than PU given its higher median and narrower IQR. Thus, in the participant-specific experiments, the darker skin group outperformed the lighter skin group when using the back side of the hand as the ROI for $SpO_2$ prediction but they were comparable when using the palm of the hand. Additionally, the side of the hand had an impact on $SpO_2$ prediction for the darker skin group but not for the lighter skin group.

Table 5 shows ablation results of Model 1 in the leave-one-participant-out setup. This table presents the medians and IQRs specified for numerical comparison. The ablation studies justify the use of (i) nonlinear channel combinations and (ii) convolutional layers for temporal feature extraction. In ablation study 1, the nonlinear channel combination may be replaced with a single linear channel combination layer with no activation function as the first variant of Model 1. In ablation study 2, we replace the convolutional layers for temporal feature extraction with fully-connected dense layers as the second variant of Model 1.

TABLE 5

Ablation studies for Model 1 in the leave-one-participant-out mode

| Method | | p | MAE (%) | RMSE (%) |
|---|---|---|---|---|
| Linear Ch. Comb. + | Median | 0.46 | 2.14 | 2.66 |
| Conv. layer for Feat Extra. | IQR | 0.38 | 0.73 | 0.93 |
| Nonlinear Ch. Comb. + | Median | 0.41 | 2.29 | 2.66 |
| Fully Connec, layer for Feat. Extra. | IQR | 0.39 | 0.63 | 0.70 |
| Model 1 (Proposed): Nonlinear Ch. | Median | 0.46 | 197 | 2.32 |
| Comb. + Conv. layer for Feat. | IQR | 0.36 | 0.80 | 0.87 |
| Extra. | | | | |

First, the first and the third rows in Table 5 were compared for ablation study 1. The Model 1 achieves a better correlation and a better RMSE than its linear channel combination variant, suggesting the necessity of using the non-linear channel combination method. Second, in ablation study 2, the second and the third rows in Table 8 were compared. As a result of the comparison, Model 1 outperformed its second variant with fully-connected layers for feature extraction with better medians in all metrics. This suggests that convolutional layers are better than fully connected layers for temporal feature extraction.

In certain embodiments, RGB combination weights may be visualized. For instance, a separate investigation was conducted to visualize the learned weights for the RGB channels. In doing so, it was possible to combine the RGB channels for SpO$_2$ prediction. Having an explainable model may be important for a physiological prediction task like this. The neural network models can be considered as nonlinear approximations of the hypothetically true function that can extract the physiological features related to SpO$_2$ buried in the RGB videos. The ratio-of-ratios method, for example, is another such extractor that combines the information from the different color channels at the end of the pipeline. For this experiment, the modified version of Model 1 was used from the ablation studies that has a single linear channel combination at the beginning. Seeing that using a single linear channel combination did not significantly reduce model performance in the ablation studies, and understanding that the linear component may dominate the Taylor expansion of a nonlinear function, only linear combinations were used for this model to facilitate more interpretable visualizations.

Figure 14:
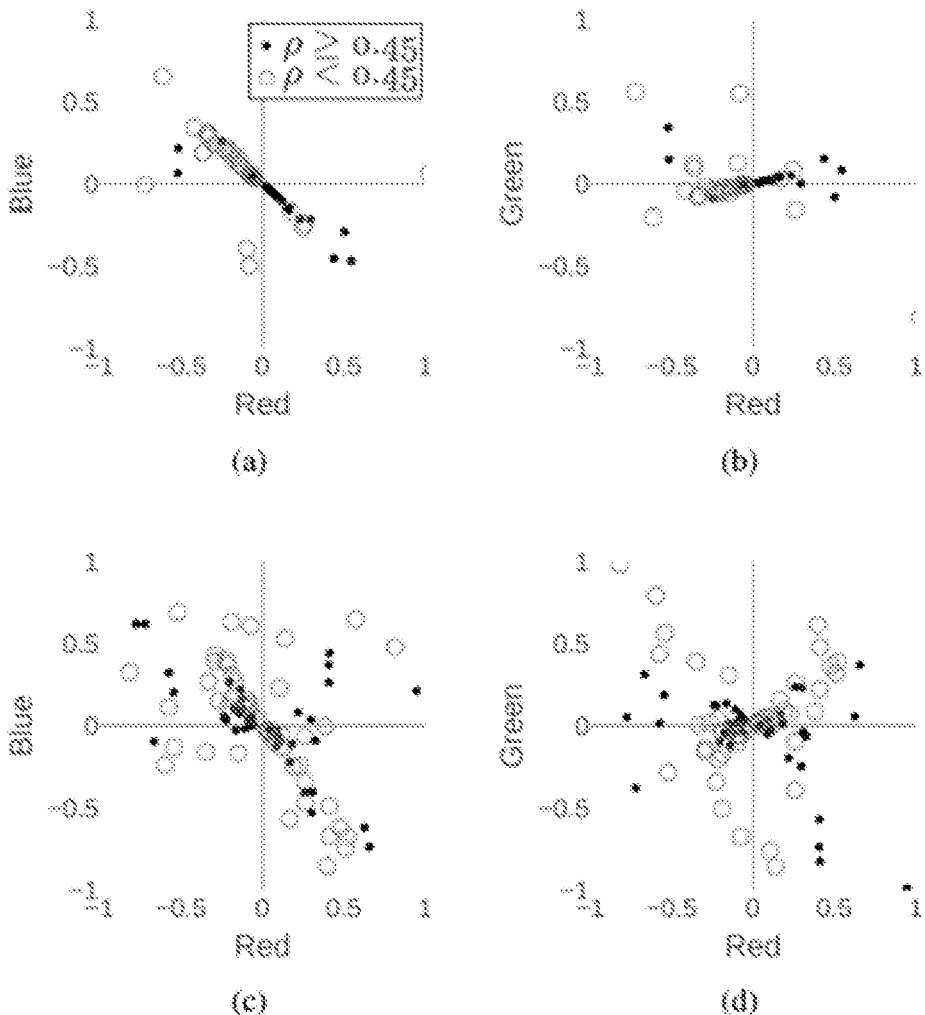
FIG. 14 illustrates plots of learned RGB channel weights, according to certain embodiments.

FIG. 14 illustrates learned RGB channel weights, according to certain embodiments. 100 different instances of the model were trained on the first two cycles from all the recordings and tested on the third cycle from all recordings. The difference between each instance is that the weights are randomly initialized. The weights for each channel learned by the model instances were visualized as points representing the heads of the linear combination vector in RGB space. Each point is colored according to the average test correlation achieved by the model instance. FIG. 14 illustrates the projections of these points onto the RB and RG planes. The subfigures reveal that the majority of the channel weights lay along certain line in the RGB space. For the weights on the line the ratio of the blue channel weight to the red channel weight is 0.87, the ratio of the green channel weight to red channel weight is 0.18. It is clear that the red and blue channels are the dominating factors for SpO$_2$ prediction.

To verify this result, this experiment was repeated. However, instead of using the data from all participants, for each model instance, seven participants were randomly selected, and their data was used for training and testing. In this case, the difference between each model instance is not only the initialized weights but also the random subset of participants that the model was trained on. FIG. 14, plot (d) reveals that most of the better performing instances have little contribution from the green channel. In plot (c), it can again be seen that most of the points lay on a line in the RB plane.

These results are in accordance with the physical understanding of how light is absorbed by hemoglobin in the blood. FIG. 9 revealed a large difference between the extinction coefficients, or the amount of light absorbed, by deoxygenated and oxygenated hemoglobin at the red wavelength. There is a significantly smaller difference at the blue wavelength and almost no difference at green. The amount of light absorbed influences the amount of light reflected which can be measured through the camera. A larger difference in extinction coefficients makes it easier to measure the ratio of light absorbed by oxygenated vs. deoxygenated hemoglobin over time. This ratio indicates the level of blood oxygen saturation. Therefore, from a physiological perspective, it makes sense for the neural networks to give larger weight to the red and then blue channels and give little to the green channel. These visualizations indicate that the models are learning physically meaningful features.

Figure 15:
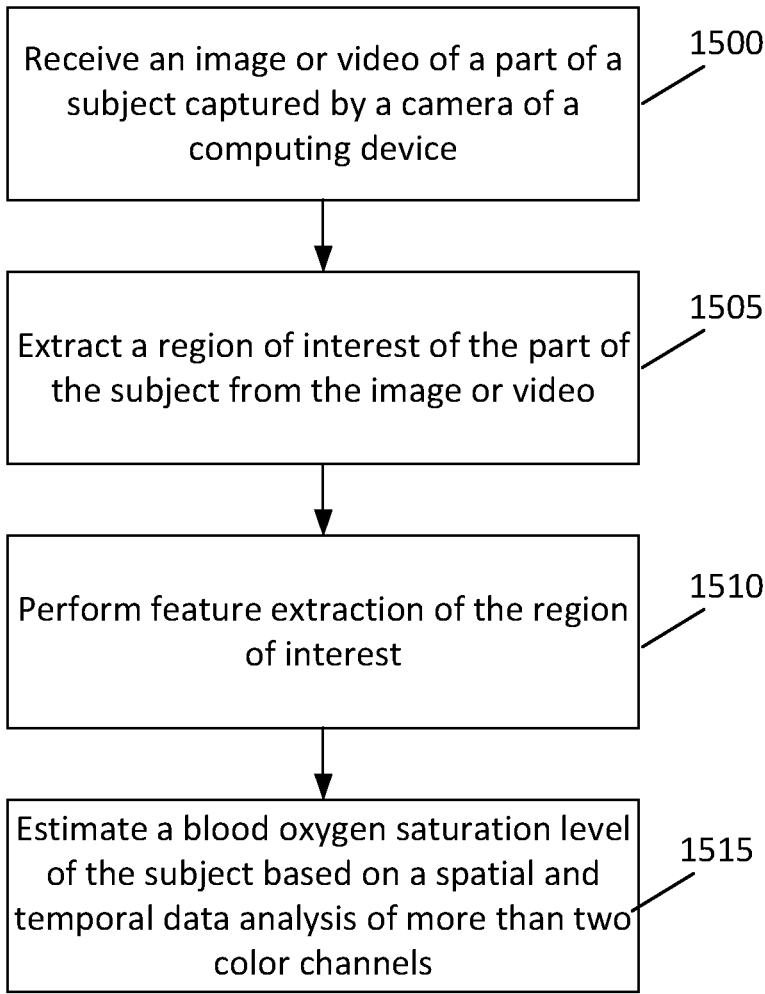
FIG. 15 illustrates an example of a flow diagram of a method, according to certain embodiments.

FIG. 15 illustrates an example flow diagram of a method, according to certain example embodiments. In certain example embodiments, the flow diagram of FIG. 15 may be performed by a computing device/hardware, computer chip, or a system that includes one or more of a computer apparatus, computer system, network, neural network, apparatus, communication device, mobile computer, mobile communication device, or other similar device(s). According to certain embodiments, each of these apparatuses of the system may be represented by, for example, an apparatus similar to apparatus 10 illustrated in FIG. 16.

According to one example embodiment, the method of FIG. 15 may include, at 1500, receiving an image or video of a part of a subject captured by a camera of a computing device. The method may also include, at 1505, extracting a region of interest of the part of the subject from the image or video. The method may further include, at 1510, performing feature extraction of the region of interest. In addition, the method may include, at 1515, estimating a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

According to certain embodiments, estimation of the blood oxygen saturation level may include implementing a multi-channel ratio-of-ratios feature vector with a narrow adaptive bandpass filter. According to other embodiments, estimation of the blood oxygen saturation level comprises implementing a neural network. According to some embodiments, the neural network may be a convolutional neural network, and estimating the blood oxygen saturation level may include feeding red, green, and blue time series data of spatial averaging into a convolutional neural network. According to further embodiments, the neural network may include a structure with at least one of feature extraction from skin color signals of the subject, and channel mixing of red, green, and blue color channels of the camera.

In certain embodiments, the method may also include performing spatial averaging of the region of interest, extracting a remote photoplethysmogram signal from the spatial averaging, and determining a heart rate of the subject from the photoplethysmogram signal. For instance, in some example embodiments, the heart rate may be determined by dynamic programming and adaptive trace compensation. In some embodiments, the method may further include calculating, based on the heart rate, DC and AC components of red, green, and blue color channels of the camera based on the spatial averaging, and generating a regression model from pairwise ratios of the spatial averaging. In other embodiments, the method may also include estimating a weight vector from the regression model. In some embodiments, the blood oxygen saturation level may be estimated based on the estimated weight vector.

Figure 16:
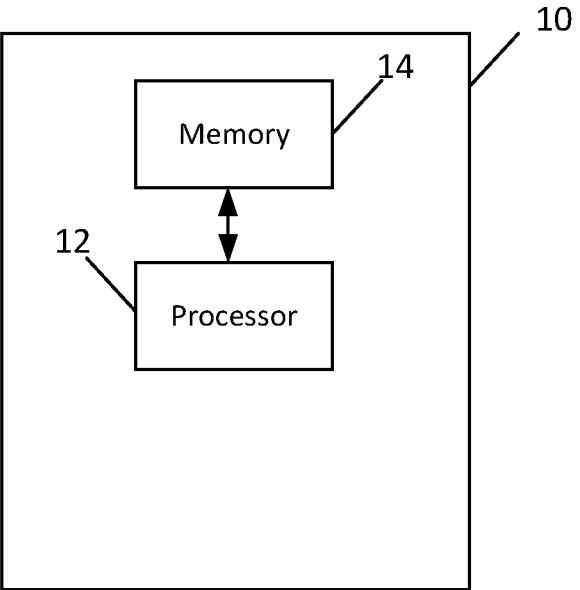
FIG. 16 illustrates an example apparatus, according to certain embodiments.

FIG. 16 illustrates an apparatus 10 according to an example embodiment. In certain embodiments, although only one apparatus 10 is illustrated, apparatus 10 may be an apparatus representing multiple apparatuses as part of a system or network. For example, in certain embodiments, apparatus 10 may be an apparatus, or chip, a communication device, a mobile computer or communication device, or computer apparatus that operates individually or together in a computer system or computer network system with other computer apparatuses.

In some embodiments, the functionality of any of the methods, processes, algorithms, or flow charts described herein may be implemented by software and/or computer program code or portions of code stored in memory or other computer-readable or tangible media and executed by a processor.

For example, in some embodiments, apparatus 10 may include one or more processors, one or more computer-readable storage mediums (for example, memory, storage, or the like), one or more radio access components (for example, a modem, a transceiver, or the like), and/or a user interface. It should be noted that one skilled in the art would understand that apparatus 10 may include components or features not shown in FIG. 16.

As illustrated in the example of FIG. 16, apparatus 10 may include or be coupled to a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. While a single processor 12 is shown in FIG. 16, multiple processors may be utilized according to other embodiments. For example, it should be understood that, in certain example embodiments, apparatus 10 may include two or more processors that may form a multiprocessor system (e.g., in this case processor 12 may represent a multiprocessor) that may support multiprocessing. According to certain example embodiments, the multiprocessor system may be tightly coupled or loosely coupled (e.g., to form a computer cluster).

Processor 12 may perform functions associated with the operation of apparatus 10 including, as some examples, precoding of antenna gain/phase parameters, encoding and decoding of individual bits forming a communication message, formatting of information, and overall control of the apparatus 10, including processes illustrated in FIGS. 1-15.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read-only memory (ROM), static storage such as a magnetic or optical disk, hard disk drive (HDD), or any other type of non-transitory machine or computer-readable media. The instructions stored in memory 14 may include program instructions or computer program code that, when executed by processor 12, enable the apparatus 10 to perform any of the various tasks described herein.

In certain embodiments, apparatus 10 may further include or be coupled to (internal or external) a drive or port that is configured to accept and read an external computer-readable storage medium, such as an optical disc, USB drive, flash drive, or any other storage medium. For example, the external computer-readable storage medium may store a computer program or software for execution by processor 12 and/or apparatus 10 to perform any of the methods illustrated in FIGS. 1-15.

Additionally or alternatively, in some embodiments, apparatus 10 may include an input and/or output device (I/O device). In certain embodiments, apparatus 10 may further include a user interface, such as a graphical user interface or touchscreen.

In certain embodiments, memory 14 stores software modules that provide functionality when executed by processor 12. The modules may include, for example, an operating system that provides operating system functionality for apparatus 10. The memory may also store one or more functional modules, such as an application or program, to provide additional functionality for apparatus 10. The components of apparatus 10 may be implemented in hardware, or as any suitable combination of hardware and software. According to certain example embodiments, processor 12 and memory 14 may be included in or may form a part of processing circuitry or control circuitry.

As used herein, the term "circuitry" may refer to hardware-only circuitry implementations (e.g., analog and/or digital circuitry), combinations of hardware circuits and software, combinations of analog and/or digital hardware circuits with software/firmware, any portions of hardware processor(s) with software (including digital signal processors) that work together to cause an apparatus (e.g., apparatus 10) to perform various functions, and/or hardware circuit(s) and/or processor(s), or portions thereof, that use software for operation but where the software may not be present when it is not needed for operation. As a further example, as used herein, the term "circuitry" may also cover an implementation of merely a hardware circuit or processor (or multiple processors), or portion of a hardware circuit or processor, and its accompanying software and/or firmware.

According to certain embodiments, apparatus 10 may be controlled by memory 14 and processor 12 to receive an image or video of a part of a subject captured by a camera of a computing device. Apparatus 10 may also be controlled by memory 14 and processor 12 to extract a region of interest of the part of the subject from the image or video. Apparatus 10 may further be controlled by memory 14 and processor 12 to perform feature extraction of the region of interest. In addition, apparatus 10 may be controlled by memory 14 and processor 12 to estimate a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

In some example embodiments, an apparatus (e.g., apparatus 10 and/or apparatus 20) may include means for performing a method, a process, or any of the variants discussed herein. Examples of the means may include one or more processors, memory, controllers, transmitters, receivers, and/or computer program code for causing the performance of the operations.

Certain example embodiments may be directed to an apparatus that includes means for receiving an image or video of a part of a subject captured by a camera of a computing device. The apparatus may also include means for extracting a region of interest of the part of the subject from the image or video. The apparatus may further include means for performing feature extraction of the region of interest. In addition, the apparatus may include means for estimating a blood oxygen saturation level of the subject based on a spatial and temporal data analysis of more than two color channels. According to certain embodiments, feature extraction and estimation of the blood oxygen saturation level may include implementing a combination of spatial averaging, color channel mixing, and temporal trend analysis.

Certain embodiments described herein provide several technical improvements, enhancements, and/or advantages. In some embodiments, it may be possible to improve the correlation coefficient from 0.22 to 0.68, and the MAE from 1.67% to 1.26%. This improvement confirms that the multi-channel feature of certain embodiments helps with more accurate $SpO_2$ monitoring. According to other embodiments, it may be possible to improve testing MAE by 18%, and improve the correlation coefficient for testing by 13%, and MAE by 9%, indicating the contribution of the narrow HR-based ABP filter. In further embodiments, it may be possible to provide accurate HR estimation for ABP filter design, and improve the quality of the AC magnitude by preserving the most cardiac-related signal from RGB channels, which in turn helps with the accurate $SpO_2$ monitoring.

A computer program product may include one or more computer-executable components which, when the program is run, are configured to carry out some example embodiments. The one or more computer-executable components may be at least one software code or portions of it. Modifications and configurations required for implementing operations of certain example embodiments may be performed as routine(s), which may be implemented as added or updated software routine(s). Software routine(s) may be downloaded into the apparatus.

As an example, software or a computer program code or portions of it may be in a source code form, object code form, or in some intermediate form, and it may be stored in some sort of carrier, distribution medium, or computer-readable medium, which may be any entity or device capable of carrying the program. Such carriers may include a record medium, computer memory, read-only memory, photoelectrical and/or electrical carrier signal, telecommunications signal, and software distribution package, for example. Depending on the processing power needed, the computer program may be executed in a single electronic digital computer or it may be distributed amongst a number of computers. The computer-readable medium or computer-readable storage medium may be a non-transitory medium.

In other example embodiments, the functionality may be performed by hardware or circuitry included in an apparatus (e.g., apparatus), for example through the use of an application-specific integrated circuit (ASIC), a programmable gate array (PGA), a field-programmable gate array (FPGA), or any other combination of hardware and software. In yet another example embodiment, the functionality may be implemented as a signal, a non-tangible means that can be carried by an electromagnetic signal downloaded from the Internet or other network.

According to an example embodiment, an apparatus, such as a device, or a corresponding component, may be configured as circuitry, a computer or a microprocessor, such as a single-chip computer element, or as a chipset, including at least a memory for providing storage capacity used for arithmetic operation and an operation processor for executing the arithmetic operation.

One having skill in the art will readily understand that the description as discussed above may be practiced with procedures in a different order, and/or with hardware elements in configurations, which are different than those which are disclosed. Therefore, although the present disclosure presents and describes certain example embodiments, it would be apparent to those of skill in the art that certain modifications, variations, and alternative constructions would be apparent while remaining within the spirit and scope of example embodiments.

PARTIAL GLOSSARY

CNN Convolutional Neural Network
HR Heart Rate
CMOS Complementary Metal-Oxide-Semiconductor
PD Palm Down
PU Palm Up
$SpO_2$ Blood Oxygen Saturation
We claim:

1. A method, comprising:
   receiving an image or video of a part of a subject captured by a camera of a computing device;
   extracting a region of interest of the part of the subject from the image or video;
   performing feature extraction of the region of interest;
   estimating a blood oxygen saturation level of the subject based on a spatial and temporal data analysis of more than two color channels, wherein feature extraction and estimation of the blood oxygen saturation level comprises implementing a combination of spatial averaging, color channel mixing, and temporal trend analysis;
   extracting a remote photoplethysmogram signal from the spatial averaging;
   determining a heart rate of the subject from the photoplethysmogram signal;
   calculating, based on the heart rate, DC and AC components of red, green, and blue color channels of the camera based on the spatial averaging; and
   generating a regression model from pairwise ratios of the spatial averaging.

2. The method according to claim 1, wherein estimation of the blood oxygen saturation level comprises implementing a multi-channel ratio-of-ratios feature vector with a narrow adaptive bandpass filter.

3. The method according to claim 1, wherein estimation of the blood oxygen saturation level comprises implementing a neural network.

4. The method according to claim 3,
   wherein the neural network is a convolutional neural network, and
   wherein estimating the blood oxygen saturation level comprises feeding red, green, and blue time series data of the spatial averaging into a convolutional neural network.

5. The method according to claim 3,
   wherein the neural network comprises a structure with at least one of feature extraction from skin color signals of the subject, and channel mixing of red, green, and blue color channels of the camera.

6. The method according to claim 1, further comprising:
   estimating a weight vector from the regression model,
   wherein the blood oxygen saturation level is estimated based on the estimated weight vector.

7. An apparatus, comprising:
   at least one processor; and
   at least one memory comprising computer program code,
   the at least one memory and the computer program code are configured, with the at least one processor, to cause the apparatus at least to receive an image or video of a part of a subject captured by a camera of a computing device;

extract a region of interest of the part of the subject from the image or video;

perform feature extraction of the region of interest;

estimate a blood oxygen saturation level of the subject based on a spatial and temporal data analysis of more than two color channels, wherein feature extraction and estimation of the blood oxygen saturation level comprises implementing a combination of spatial averaging, color channel mixing, and temporal trend analysis;

extract a remote photoplethysmogram signal from the spatial averaging;

determine a heart rate of the subject from the photoplethysmogram signal;

calculate, based on the heart rate, DC and AC components of red, green, and blue color channels of the camera based on the spatial averaging; and generate a regression model from pairwise ratios of the spatial averaging.

8. The apparatus according to claim 7, wherein estimation of the blood oxygen saturation level comprises implementing a multi-channel ratio-of-ratios feature vector with a narrow adaptive bandpass filter.

9. The Apparatus according to claim 7, wherein estimation of the blood oxygen saturation level comprises implementing a neural network.

10. The apparatus according to claim 9, wherein the neural network is a convolutional neural network, and wherein estimating the blood oxygen saturation level comprises feeding red, green, and blue time series data of the spatial averaging into a convolutional neural network.

11. The apparatus according to claim 9, wherein the neural network comprises a structure with at least one of feature extraction from skin color signals of the subject, and channel mixing of red, green, and blue color channels of the camera.

12. The apparatus according to claim 7, wherein the at least one memory and the computer program code are further configured, with the at least one processor, to cause the apparatus at least to:

estimate a weight vector from the regression model, wherein the blood oxygen saturation level is estimated based on the estimated weight vector.

13. A computer program, embodied on a non-transitory computer readable medium, the computer program comprising computer executable code, which, when executed by a processor, causes the processor to:

receive an image or video of a part of a subject captured by a camera of a computing device;

extract a region of interest of the part of the subject from the image or video;

perform feature extraction of the region of interest;

estimate a blood oxygen saturation level of the subject based on a spatial and temporal data analysis of more than two color channels, wherein feature extraction and estimation of the blood oxygen saturation level comprises implementing a combination of spatial averaging, color channel mixing, and temporal trend analysis;

extract a remote photoplethysmogram signal from the spatial averaging;

determine a heart rate of the subject from the photoplethysmogram signal;

calculate, based on the heart rate, DC and AC components of red, green, and blue color channels of the camera based on the spatial averaging; and generate a regression model from pairwise ratios of the spatial averaging.

14. The computer program according to claim 13, wherein estimation of the blood oxygen saturation level comprises implementing a multi-channel ratio-of-ratios feature vector with a narrow adaptive bandpass filter.

15. The computer program according to claim 13, wherein estimation of the blood oxygen saturation level comprises implementing a neural network.

16. The computer program according to claim 15, wherein the neural network is a convolutional neural network, and wherein estimating the blood oxygen saturation level comprises feeding red, green, and blue time series data of the spatial averaging into a convolutional neural network.

17. The computer program according to claim 15, wherein the neural network comprises a structure with at least one of feature extraction from skin color signals of the subject, and channel mixing of red, green, and blue color channels of the camera.

18. The computer program according to claim 13, wherein the processor is further caused to:

estimate a weight vector from the regression model, wherein the blood oxygen saturation level is estimated based on the estimated weight vector.

\* \* \* \* \*